(12) United States Patent
Iceman et al.

(10) Patent No.: US 9,393,002 B2
(45) Date of Patent: Jul. 19, 2016

(54) CLIP FOR IMPLANT DEPLOYMENT DEVICE

(71) Applicant: Covidien LP, Mansfield, MA (US)

(72) Inventors: Jason T. Iceman, Cheshire, CT (US); David Batty, West Hartford, CT (US); Mitchell Palmer, Wake Forest, NC (US); Ofek Levin, Moshav Amirim (IL); Arie Levy, Ramat-Gan (IL)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/951,499

(22) Filed: Jul. 26, 2013

(65) Prior Publication Data

US 2013/0310637 A1    Nov. 21, 2013

Related U.S. Application Data

(63) Continuation-in-part of application No. 13/451,962, filed on Apr. 20, 2012, now Pat. No. 8,753,361, which is a continuation-in-part of application No. 12/891,962, filed on Sep. 28, 2010, now Pat. No.

(Continued)

(51) Int. Cl.
  *A61B 17/00* (2006.01)
  *A61F 2/00* (2006.01)
  *A61B 17/064* (2006.01)
  *A61B 17/068* (2006.01)

(52) U.S. Cl.
  CPC ......... *A61B 17/00234* (2013.01); *A61F 2/0063* (2013.01); *A61B 17/064* (2013.01); *A61B 17/0643* (2013.01); *A61B 17/0686* (2013.01); *A61B 2017/00292* (2013.01); *A61F 2002/0072* (2013.01); *A61F 2220/0016* (2013.01)

(58) Field of Classification Search
  CPC ................. A61F 2/0063; A61F 2002/0072
  See application file for complete search history.

(56) References Cited

U.S. PATENT DOCUMENTS

| | | |
|---|---|---|
| 4,347,847 A | 9/1982 | Usher |
| 4,400,833 A | 8/1983 | Kurland |
| 4,452,245 A | 6/1984 | Usher |
| 4,485,816 A | 12/1984 | Krumme |
| 4,585,458 A | 4/1986 | Kurland |
| 4,633,873 A | 1/1987 | Dumican |
| 4,838,884 A | 6/1989 | Dumican |

(Continued)

FOREIGN PATENT DOCUMENTS

| | | |
|---|---|---|
| CA | 2413904 | 10/2003 |
| EP | 0328421 | 8/1989 |

(Continued)

OTHER PUBLICATIONS

Extended European Search Report corresponding to EP 13 18 1252.1, completed Nov. 12, 2013 and mailed Nov. 21, 2013; (8 pp).

(Continued)

*Primary Examiner* — Todd J Scherbel

(57) ABSTRACT

A surgical device for deploying a surgical implant includes a proximal portion and a distal portion. The distal portion includes a frame arm. A spring clip system is coupled to the frame arm and includes a pair of clips and a spring member. The spring member is connected to each of the clips and biases the clips towards a closed position. In the closed position, the clips are configured to retain the implant in contact with the frame arm.

7 Claims, 22 Drawing Sheets

Related U.S. Application Data 8,758,373, which is a continuation-in-part of application No. 12/834,456, filed on Jul. 12, 2010, now Pat. No. 8,753,359, which is a continuation-in-part of application No. PCT/IL2009/000188, filed on Feb. 18, 2009.

(60) Provisional application No. 61/691,859, filed on Aug. 22, 2012, provisional application No. 61/691,860, filed on Aug. 22, 2012, provisional application No. 61/691,863, filed on Aug. 22, 2012, provisional application No. 61/691,864, filed on Aug. 22, 2012, provisional application No. 61/691,866, filed on Aug. 22, 2012, provisional application No. 61/691,869, filed on Aug. 22, 2012, provisional application No. 61/302,186, filed on Feb. 8, 2010, provisional application No. 61/029,386, filed on Feb. 18, 2008.

(56) References Cited

U.S. PATENT DOCUMENTS

| | | |
|---|---|---|
| 4,854,316 A | 8/1989 | Davis |
| 4,930,674 A | 6/1990 | Barak |
| 5,019,096 A | 5/1991 | Fox, Jr. |
| 5,116,357 A | 5/1992 | Eberbach |
| 5,122,155 A | 6/1992 | Eberbach |
| 5,125,553 A | 6/1992 | Oddsen |
| 5,141,515 A | 8/1992 | Eberbach |
| 5,147,374 A | 9/1992 | Fernandez |
| 5,176,692 A | 1/1993 | Wilk |
| 5,203,864 A | 4/1993 | Phillips |
| 5,219,077 A | 6/1993 | Transue |
| 5,249,682 A | 10/1993 | Transue |
| 5,254,133 A | 10/1993 | Seid |
| 5,258,000 A | 11/1993 | Gianturco |
| 5,263,969 A | 11/1993 | Phillips |
| 5,289,963 A | 3/1994 | McGarry |
| 5,290,217 A | 3/1994 | Campos |
| 5,292,328 A | 3/1994 | Hain |
| 5,304,187 A | 4/1994 | Green |
| 5,333,624 A | 8/1994 | Tovey |
| 5,354,292 A | 10/1994 | Braeuer |
| 5,356,064 A | 10/1994 | Green |
| 5,356,432 A | 10/1994 | Rutkow |
| 5,364,002 A | 11/1994 | Green |
| 5,364,004 A | 11/1994 | Davidson |
| 5,366,460 A | 11/1994 | Eberbach |
| 5,368,602 A | 11/1994 | de la Torre |
| 5,370,650 A | 12/1994 | Tovey |
| 5,376,097 A | 12/1994 | Phillips |
| 5,383,477 A | 1/1995 | DeMatteis |
| 5,392,978 A | 2/1995 | Velez |
| 5,397,331 A | 3/1995 | Himpens |
| 5,397,332 A | 3/1995 | Kammerer |
| 5,405,360 A | 4/1995 | Tovey |
| 5,425,357 A | 6/1995 | Moll |
| 5,425,740 A | 6/1995 | Hutchinson |
| 5,433,996 A | 7/1995 | Kranzler |
| 5,464,403 A | 11/1995 | Kieturakis |
| 5,497,933 A | 3/1996 | Defonzo |
| 5,531,759 A | 7/1996 | Kensey |
| 5,560,224 A | 10/1996 | Tessler |
| 5,560,532 A | 10/1996 | DeFonzo |
| 5,564,615 A | 10/1996 | Bishop |
| 5,569,273 A | 10/1996 | Titone |
| 5,577,654 A | 11/1996 | Bishop |
| 5,588,580 A | 12/1996 | Paul |
| 5,588,581 A | 12/1996 | Conlon |
| 5,601,224 A | 2/1997 | Bishop |
| 5,614,284 A | 3/1997 | Kranzler |
| 5,618,290 A | 4/1997 | Toy |
| 5,626,587 A | 5/1997 | Bishop |
| 5,634,584 A | 6/1997 | Okorocha |
| 5,634,931 A | 6/1997 | Kugel |
| 5,653,718 A * | 8/1997 | Yoon .................. 606/148 |
| 5,662,662 A | 9/1997 | Bishop |
| 5,695,525 A | 12/1997 | Mulhauser |
| 5,716,409 A | 2/1998 | Debbas |
| 5,725,577 A | 3/1998 | Saxon |
| 5,728,119 A | 3/1998 | Smith |
| 5,749,895 A | 5/1998 | Sawyer |
| 5,766,246 A | 6/1998 | Mulhauser |
| 5,769,864 A | 6/1998 | Kugel |
| 5,779,728 A | 7/1998 | Lunsford |
| 5,810,851 A | 9/1998 | Yoon |
| 5,814,058 A | 9/1998 | Carlson |
| 5,817,109 A | 10/1998 | McGarry |
| 5,824,082 A | 10/1998 | Brown |
| 5,836,961 A | 11/1998 | Kieturakis |
| 5,854,383 A | 12/1998 | Erneta |
| 5,863,531 A | 1/1999 | Naughton |
| 5,865,728 A | 2/1999 | Moll |
| 5,911,726 A | 6/1999 | Belknap |
| 5,916,225 A | 6/1999 | Kugel |
| 5,925,058 A | 7/1999 | Smith |
| 5,951,997 A | 9/1999 | Bezwada |
| 5,954,767 A | 9/1999 | Pajotin |
| 5,972,007 A | 10/1999 | Sheffield |
| 5,972,008 A | 10/1999 | Kalinski |
| 5,990,378 A | 11/1999 | Ellis |
| 6,004,333 A | 12/1999 | Sheffield |
| 6,042,592 A | 3/2000 | Schmitt |
| 6,066,776 A | 5/2000 | Goodwin |
| 6,066,777 A | 5/2000 | Benchetrit |
| 6,090,116 A | 7/2000 | D'Aversa |
| 6,113,609 A | 9/2000 | Adams |
| 6,113,611 A | 9/2000 | Allen |
| 6,113,624 A | 9/2000 | Bezwada |
| 6,166,286 A | 12/2000 | Trabucco |
| 6,171,318 B1 | 1/2001 | Kugel |
| 6,174,320 B1 | 1/2001 | Kugel |
| 6,176,863 B1 | 1/2001 | Kugel |
| 6,197,036 B1 | 3/2001 | Tripp |
| 6,214,020 B1 | 4/2001 | Mulhauser |
| 6,224,616 B1 | 5/2001 | Kugel |
| 6,241,768 B1 | 6/2001 | Agarwal |
| 6,258,113 B1 | 7/2001 | Adams |
| 6,258,124 B1 | 7/2001 | Darois |
| 6,267,772 B1 | 7/2001 | Mulhauser |
| 6,273,903 B1 * | 8/2001 | Wilk .................. A61B 17/083 606/142 |
| 6,280,453 B1 | 8/2001 | Kugel |
| 6,287,316 B1 | 9/2001 | Agarwal |
| 6,290,708 B1 | 9/2001 | Kugel |
| 6,312,442 B1 | 11/2001 | Kieturakis |
| 6,319,264 B1 | 11/2001 | Tormala |
| 6,368,541 B1 | 4/2002 | Pajotin |
| 6,375,662 B1 | 4/2002 | Schmitt |
| 6,383,201 B1 | 5/2002 | Dong |
| 6,391,060 B1 | 5/2002 | Ory |
| 6,408,656 B1 | 6/2002 | Ory |
| 6,416,486 B1 | 7/2002 | Wampler |
| 6,425,900 B1 | 7/2002 | Knodel |
| 6,425,924 B1 | 7/2002 | Rousseau |
| 6,436,030 B2 | 8/2002 | Rehil |
| 6,447,524 B1 | 9/2002 | Knodel |
| 6,478,803 B1 | 11/2002 | Kapec |
| 6,485,503 B2 | 11/2002 | Jacobs |
| 6,497,650 B1 | 12/2002 | Nicolo |
| 6,517,584 B1 | 2/2003 | Lecalve |
| 6,527,785 B2 | 3/2003 | Sancoff |
| 6,551,241 B1 | 4/2003 | Schultz |
| 6,551,333 B2 | 4/2003 | Kuhns |
| 6,558,400 B2 | 5/2003 | Deem |
| 6,565,590 B2 | 5/2003 | Kieturakis |
| 6,575,988 B2 | 6/2003 | Rousseau |
| 6,607,541 B1 | 8/2003 | Gardiner |
| 6,610,006 B1 | 8/2003 | Amid |
| 6,613,059 B2 | 9/2003 | Schaller |
| 6,613,072 B2 | 9/2003 | Lau |
| 6,616,685 B2 | 9/2003 | Rousseau |
| 6,638,208 B1 | 10/2003 | Natarajan |
| 6,638,284 B1 | 10/2003 | Rousseau |

(56) References Cited

U.S. PATENT DOCUMENTS

| | | |
|---|---|---|
| 6,638,292 B2 | 10/2003 | Adams |
| 6,638,297 B1 | 10/2003 | Huitema |
| 6,652,595 B1 | 11/2003 | Nicolo |
| 6,666,817 B2 | 12/2003 | Li |
| 6,669,706 B2 | 12/2003 | Schmitt |
| 6,669,735 B1 | 12/2003 | Pelissier |
| 6,676,643 B2 | 1/2004 | Brushey |
| 6,689,047 B2 | 2/2004 | Gellman |
| 6,694,192 B2 | 2/2004 | Policker |
| 6,695,856 B2 | 2/2004 | Kieturakis |
| 6,709,442 B2 | 3/2004 | Miller |
| 6,736,823 B2 | 5/2004 | Darois |
| 6,736,854 B2 | 5/2004 | Vadurro |
| 6,737,371 B1 | 5/2004 | Planck |
| 6,746,458 B1 | 6/2004 | Cloud |
| 6,755,867 B2 | 6/2004 | Rousseau |
| 6,773,438 B1 | 8/2004 | Knodel |
| 6,783,554 B2 | 8/2004 | Amara |
| 6,790,213 B2 | 9/2004 | Cherok |
| 6,800,081 B2 | 10/2004 | Parodi |
| 6,800,082 B2 | 10/2004 | Rousseau |
| 6,805,669 B2 | 10/2004 | Swanbom |
| 6,833,408 B2 | 12/2004 | Sehl |
| 6,837,893 B2 | 1/2005 | Miller |
| 6,893,452 B2 | 5/2005 | Jacobs |
| 6,913,607 B2 | 7/2005 | Ainsworth |
| 6,913,622 B2 | 7/2005 | Gjunter |
| 6,936,052 B2 | 8/2005 | Gellman |
| 6,945,980 B2 | 9/2005 | Nguyen |
| 6,953,428 B2 | 10/2005 | Gellman |
| 6,960,217 B2 | 11/2005 | Bolduc |
| 6,960,233 B1 | 11/2005 | Berg |
| 6,966,916 B2 | 11/2005 | Kumar |
| 6,974,586 B2 | 12/2005 | Greenhalgh |
| 6,991,597 B2 | 1/2006 | Gellman |
| 7,001,405 B2 | 2/2006 | Kieturakis |
| 7,011,688 B2 | 3/2006 | Gryska |
| 7,025,772 B2 | 4/2006 | Gellman |
| 7,049,345 B2 | 5/2006 | Holmes-Farley |
| 7,077,850 B2 | 7/2006 | Kortenbach |
| 7,083,629 B2 | 8/2006 | Weller |
| 7,083,630 B2 | 8/2006 | DeVries |
| 7,094,261 B2 | 8/2006 | Zotti |
| 7,101,366 B2 | 9/2006 | Trout, III |
| 7,101,381 B2 | 9/2006 | Ford |
| 7,119,062 B1 | 10/2006 | Alvis |
| 7,148,315 B2 | 12/2006 | Erneta |
| 7,198,046 B1 | 4/2007 | Argenta |
| 7,214,236 B2 | 5/2007 | Kieturakis |
| 7,216,651 B2 | 5/2007 | Argenta |
| 7,220,282 B2 | 5/2007 | Kuslich |
| 7,229,452 B2 | 6/2007 | Kayan |
| 7,235,043 B2 | 6/2007 | Gellman |
| 7,235,295 B2 | 6/2007 | Laurencin |
| 7,255,675 B2 | 8/2007 | Gertner |
| 7,320,325 B2 | 1/2008 | Duchon |
| 7,331,199 B2 | 2/2008 | Ory |
| 7,381,225 B2 | 6/2008 | Croce |
| 7,404,819 B1 | 7/2008 | Darios |
| 7,406,969 B2 | 8/2008 | Duchon |
| 7,407,480 B2 | 8/2008 | Staskin |
| 7,485,129 B2 | 2/2009 | Eisenkolb |
| 7,491,232 B2 | 2/2009 | Bolduc |
| 7,500,945 B2 | 3/2009 | Cox |
| 7,500,993 B2 | 3/2009 | De La Torre |
| 7,524,333 B2 | 4/2009 | Lambrecht |
| 7,544,213 B2 | 6/2009 | Adams |
| 7,553,329 B2 | 6/2009 | Lambrecht |
| 7,553,330 B2 | 6/2009 | Lambrecht |
| RE40,833 E | 7/2009 | Wintermantel |
| 7,566,337 B2 | 7/2009 | Sogaard-Andersen |
| 7,594,921 B2 | 9/2009 | Browning |
| 7,601,118 B2 | 10/2009 | Smith |
| 7,601,172 B2 | 10/2009 | Segal |
| 7,819,797 B2 | 10/2010 | Vanden Hoek |
| 8,097,008 B2 | 1/2012 | Henderson |
| 2001/0016754 A1 | 8/2001 | Adams |
| 2001/0018592 A1 | 8/2001 | Schaller |
| 2001/0018593 A1 | 8/2001 | Nguyen |
| 2001/0027347 A1 | 10/2001 | Rousseau |
| 2001/0044637 A1 | 11/2001 | Jacobs |
| 2001/0049538 A1 | 12/2001 | Trabucco |
| 2001/0049539 A1 | 12/2001 | Rehil |
| 2001/0053919 A1 | 12/2001 | Kieturakis |
| 2001/0056275 A1 | 12/2001 | Brushey |
| 2002/0010457 A1 | 1/2002 | Duchon |
| 2002/0010480 A1 | 1/2002 | Sancoff |
| 2002/0010490 A1 | 1/2002 | Schaller |
| 2002/0010494 A1 | 1/2002 | Policker |
| 2002/0029048 A1 | 3/2002 | Miller |
| 2002/0042658 A1 | 4/2002 | Tyagi |
| 2002/0049503 A1 | 4/2002 | Milbocker |
| 2002/0049504 A1 | 4/2002 | Barault |
| 2002/0052612 A1 | 5/2002 | Schmitt |
| 2002/0052654 A1 | 5/2002 | Darois |
| 2002/0058967 A1 | 5/2002 | Jervis |
| 2002/0065524 A1 | 5/2002 | Miller |
| 2002/0066360 A1 | 6/2002 | Greenhalgh |
| 2002/0077652 A1 | 6/2002 | Kieturakis |
| 2002/0082621 A1 | 6/2002 | Schurr |
| 2002/0087170 A1 | 7/2002 | Kuhns |
| 2002/0091405 A1 | 7/2002 | Kieturakis |
| 2002/0103434 A1 | 8/2002 | Swanbom |
| 2002/0103494 A1 | 8/2002 | Pacey |
| 2002/0107539 A1 | 8/2002 | Kieturakis |
| 2002/0116070 A1 | 8/2002 | Amara |
| 2002/0117534 A1 | 8/2002 | Green |
| 2002/0147457 A1 | 10/2002 | Rosseau |
| 2002/0165561 A1 | 11/2002 | Ainsworth |
| 2002/0169452 A1 | 11/2002 | Tormala |
| 2002/0173803 A1 | 11/2002 | Ainsworth |
| 2002/0173804 A1 | 11/2002 | Rousseau |
| 2002/0183765 A1 | 12/2002 | Adams |
| 2002/0183768 A1 | 12/2002 | Deem |
| 2002/0188317 A1 | 12/2002 | Rousseau |
| 2003/0004581 A1 | 1/2003 | Rousseau |
| 2003/0039626 A1 | 2/2003 | Holmes-Farley |
| 2003/0065359 A1 | 4/2003 | Weller |
| 2003/0073976 A1 | 4/2003 | Brushey |
| 2003/0078602 A1 | 4/2003 | Rousseau |
| 2003/0078603 A1 | 4/2003 | Schaller |
| 2003/0105473 A1 | 6/2003 | Miller |
| 2003/0109892 A1 | 6/2003 | Deem |
| 2003/0119985 A1 | 6/2003 | Sehl |
| 2003/0120265 A1 | 6/2003 | Deem |
| 2003/0120299 A1 | 6/2003 | Kieturakis |
| 2003/0130745 A1 | 7/2003 | Cherok |
| 2003/0166628 A1 | 9/2003 | Doyle |
| 2003/0171761 A1 | 9/2003 | Sancoff |
| 2003/0171812 A1 | 9/2003 | Grunberg |
| 2003/0171823 A1 | 9/2003 | Zotti |
| 2003/0187516 A1 | 10/2003 | Amid |
| 2003/0195531 A1 | 10/2003 | Gardiner |
| 2003/0208211 A1 | 11/2003 | Kortenbach |
| 2003/0212460 A1 | 11/2003 | Darois |
| 2003/0212461 A1 | 11/2003 | Vadurro |
| 2003/0212462 A1 | 11/2003 | Gryska |
| 2003/0220660 A1 | 11/2003 | Kortenbach |
| 2003/0225355 A1 | 12/2003 | Butler |
| 2003/0225420 A1 | 12/2003 | Wardle |
| 2004/0002679 A1 | 1/2004 | Trout |
| 2004/0010317 A1 | 1/2004 | Lambrecht |
| 2004/0019360 A1 | 1/2004 | Farnsworth |
| 2004/0024386 A1 | 2/2004 | Deem |
| 2004/0024465 A1 | 2/2004 | Lambrecht |
| 2004/0030217 A1 | 2/2004 | Yeung |
| 2004/0039453 A1 | 2/2004 | Anderson |
| 2004/0044364 A1 | 3/2004 | DeVries |
| 2004/0044412 A1 | 3/2004 | Lambrecht |
| 2004/0049227 A1 | 3/2004 | Jervis |
| 2004/0049282 A1 | 3/2004 | Gjunter |
| 2004/0054376 A1 | 3/2004 | Ory |
| 2004/0059356 A1 | 3/2004 | Gingras |
| 2004/0064131 A1 | 4/2004 | Brushey |

(56) References Cited

U.S. PATENT DOCUMENTS

| | | |
|---|---|---|
| 2004/0073237 A1 | 4/2004 | Leinsing |
| 2004/0073257 A1 | 4/2004 | Spitz |
| 2004/0082755 A1 | 4/2004 | Erneta |
| 2004/0087970 A1 | 5/2004 | Chu |
| 2004/0087979 A1 | 5/2004 | Field |
| 2004/0087980 A1 | 5/2004 | Ford |
| 2004/0092937 A1 | 5/2004 | Criscuolo |
| 2004/0092969 A1 | 5/2004 | Kumar |
| 2004/0092970 A1 | 5/2004 | Xavier |
| 2004/0097924 A1 | 5/2004 | Lambrecht |
| 2004/0097986 A1 | 5/2004 | Adams |
| 2004/0122452 A1 | 6/2004 | Deem |
| 2004/0122453 A1 | 6/2004 | Deem |
| 2004/0133214 A1 | 7/2004 | Kayan |
| 2004/0144395 A1 | 7/2004 | Evans |
| 2004/0152977 A1 | 8/2004 | Duchon |
| 2004/0152978 A1 | 8/2004 | Duchon |
| 2004/0172048 A1 | 9/2004 | Browning |
| 2004/0181288 A1 | 9/2004 | Darois |
| 2004/0193043 A1 | 9/2004 | Duchon |
| 2004/0215219 A1 | 10/2004 | Eldridge |
| 2004/0225247 A1 | 11/2004 | Pugsley |
| 2004/0225373 A1 | 11/2004 | Pugsley |
| 2004/0230208 A1 | 11/2004 | Shayani |
| 2004/0234576 A1 | 11/2004 | Martin |
| 2004/0249412 A1 | 12/2004 | Snow |
| 2004/0254592 A1 | 12/2004 | DiCarlo |
| 2005/0004427 A1 | 1/2005 | Cervigni |
| 2005/0010239 A1 | 1/2005 | Chefitz |
| 2005/0010306 A1 | 1/2005 | Priewe |
| 2005/0015102 A1 | 1/2005 | Chefitz |
| 2005/0019436 A1 | 1/2005 | Burch |
| 2005/0021058 A1 | 1/2005 | Negro |
| 2005/0027369 A1 | 2/2005 | Eldridge |
| 2005/0033318 A1 | 2/2005 | Miller |
| 2005/0038452 A1 | 2/2005 | Chu |
| 2005/0054771 A1 | 3/2005 | Sehl |
| 2005/0055097 A1 | 3/2005 | Grunberg |
| 2005/0060038 A1 | 3/2005 | Lambrecht |
| 2005/0065072 A1 | 3/2005 | Keeler |
| 2005/0075667 A1 | 4/2005 | Schaller |
| 2005/0080454 A1 | 4/2005 | Drews |
| 2005/0113849 A1 | 5/2005 | Popadiuk |
| 2005/0113858 A1 | 5/2005 | Deutsch |
| 2005/0118239 A1 | 6/2005 | Sabesan |
| 2005/0129733 A1 | 6/2005 | Milbocker |
| 2005/0142315 A1 | 6/2005 | DeSimone |
| 2005/0143817 A1 | 6/2005 | Hunter |
| 2005/0149072 A1 | 7/2005 | DeVries |
| 2005/0149080 A1 | 7/2005 | Hunter |
| 2005/0149158 A1 | 7/2005 | Hunter |
| 2005/0154361 A1 | 7/2005 | Sabesan |
| 2005/0159777 A1 | 7/2005 | Spitz |
| 2005/0165425 A1 | 7/2005 | Croce |
| 2005/0165488 A1 | 7/2005 | Hunter |
| 2005/0169959 A1 | 8/2005 | Hunter |
| 2005/0175663 A1 | 8/2005 | Hunter |
| 2005/0177225 A1 | 8/2005 | Hunter |
| 2005/0181008 A1 | 8/2005 | Hunter |
| 2005/0181011 A1 | 8/2005 | Hunter |
| 2005/0181977 A1 | 8/2005 | Hunter |
| 2005/0183728 A1 | 8/2005 | Hunter |
| 2005/0191331 A1 | 9/2005 | Hunter |
| 2005/0192600 A1 | 9/2005 | Nicolo |
| 2005/0202067 A1 | 9/2005 | Lendlein |
| 2005/0222591 A1 | 10/2005 | Gingras |
| 2005/0228408 A1 | 10/2005 | Fricke |
| 2005/0234557 A1 | 10/2005 | Lambrecht |
| 2005/0240269 A1 | 10/2005 | Lambrecht |
| 2005/0244455 A1 | 11/2005 | Greenawalt |
| 2005/0245787 A1 | 11/2005 | Cox |
| 2005/0249770 A1 | 11/2005 | Hunter |
| 2005/0267325 A1 | 12/2005 | Bouchier |
| 2005/0271794 A1 | 12/2005 | DeSimone |
| 2005/0273146 A1 | 12/2005 | DeSimone |
| 2005/0283119 A1* | 12/2005 | Uth et al. ............ 604/175 |
| 2005/0283189 A1 | 12/2005 | Rosenblatt |
| 2005/0283190 A1 | 12/2005 | Huitema |
| 2005/0283246 A1 | 12/2005 | Cauthen |
| 2005/0283962 A1 | 12/2005 | Boudjemline |
| 2005/0288691 A1 | 12/2005 | Leiboff |
| 2005/0288775 A1 | 12/2005 | Dong |
| 2006/0009802 A1 | 1/2006 | Modesitt |
| 2006/0015142 A1 | 1/2006 | Malazgirt |
| 2006/0015143 A1 | 1/2006 | Alvarado |
| 2006/0024238 A1 | 2/2006 | Barth |
| 2006/0025649 A1 | 2/2006 | Smith |
| 2006/0039896 A1 | 2/2006 | Kleinsek |
| 2006/0047180 A1 | 3/2006 | Hegde |
| 2006/0052816 A1 | 3/2006 | Bates |
| 2006/0064175 A1 | 3/2006 | Pelissier |
| 2006/0079558 A1 | 4/2006 | Aberg |
| 2006/0079559 A1 | 4/2006 | Aberg |
| 2006/0083710 A1 | 4/2006 | Joerger |
| 2006/0105026 A1 | 5/2006 | Fortune |
| 2006/0116696 A1 | 6/2006 | Odermatt |
| 2006/0122637 A1 | 6/2006 | Barker |
| 2006/0127353 A1 | 6/2006 | Holmes-Farley |
| 2006/0129152 A1 | 6/2006 | Shipp |
| 2006/0129154 A1 | 6/2006 | Shipp |
| 2006/0142787 A1 | 6/2006 | Weller |
| 2006/0147488 A1 | 7/2006 | Wohlert |
| 2006/0147492 A1 | 7/2006 | Hunter |
| 2006/0149316 A1 | 7/2006 | DeVries |
| 2006/0155165 A1 | 7/2006 | Vanden Hoek |
| 2006/0155379 A1 | 7/2006 | Heneveld |
| 2006/0177489 A1 | 8/2006 | Massouda |
| 2006/0189918 A1 | 8/2006 | Barker |
| 2006/0200246 A1 | 9/2006 | Lambrecht |
| 2006/0206118 A1 | 9/2006 | Kim |
| 2006/0206178 A1 | 9/2006 | Kim |
| 2006/0210602 A1 | 9/2006 | Sehl |
| 2006/0217812 A1 | 9/2006 | Lambrecht |
| 2006/0228391 A1 | 10/2006 | Seyedin |
| 2006/0233852 A1 | 10/2006 | Milbocker |
| 2006/0240063 A9 | 10/2006 | Hunter |
| 2006/0251702 A1 | 11/2006 | Janis |
| 2006/0253203 A1 | 11/2006 | Alvarado |
| 2006/0264698 A1 | 11/2006 | Kondonis |
| 2006/0282103 A1 | 12/2006 | Fricke |
| 2006/0282105 A1 | 12/2006 | Ford |
| 2006/0287729 A1 | 12/2006 | Segal |
| 2006/0287730 A1 | 12/2006 | Segal |
| 2007/0016300 A1 | 1/2007 | Kuslich |
| 2007/0021756 A1 | 1/2007 | Kortenbach |
| 2007/0026043 A1 | 2/2007 | Guan |
| 2007/0027358 A1 | 2/2007 | Gertner |
| 2007/0032881 A1 | 2/2007 | Browning |
| 2007/0036876 A1 | 2/2007 | Burch |
| 2007/0038220 A1 | 2/2007 | Shipp |
| 2007/0038310 A1 | 2/2007 | Guetty |
| 2007/0100355 A1 | 5/2007 | Bonde |
| 2007/0110786 A1 | 5/2007 | Tenney |
| 2007/0111937 A1 | 5/2007 | Pickar |
| 2007/0118133 A1 | 5/2007 | Lambrecht |
| 2007/0118158 A1 | 5/2007 | Deem |
| 2007/0118159 A1 | 5/2007 | Deem |
| 2007/0122425 A1 | 5/2007 | Keeler |
| 2007/0134292 A1 | 6/2007 | Suokas |
| 2007/0135929 A1 | 6/2007 | Williams |
| 2007/0156245 A1 | 7/2007 | Cauthen |
| 2007/0162030 A1 | 7/2007 | Aranyi |
| 2007/0162135 A1 | 7/2007 | Segal |
| 2007/0167963 A1 | 7/2007 | Deem |
| 2007/0173864 A1 | 7/2007 | Chu |
| 2007/0173888 A1 | 7/2007 | Gertner |
| 2007/0179335 A1 | 8/2007 | Gertner |
| 2007/0184277 A1 | 8/2007 | Schussler |
| 2007/0185506 A1 | 8/2007 | Jackson |
| 2007/0185541 A1 | 8/2007 | DiUbaldi |
| 2007/0198040 A1 | 8/2007 | Buevich |
| 2007/0202148 A1 | 8/2007 | Ringeisen |
| 2007/0202173 A1 | 8/2007 | Cueto-Garcia |
| 2007/0203507 A1 | 8/2007 | McLaughlin |

(56) References Cited

U.S. PATENT DOCUMENTS

| | | |
|---|---|---|
| 2007/0207186 A1 | 9/2007 | Scanlon |
| 2007/0208358 A1 | 9/2007 | Kayan |
| 2007/0219569 A1 | 9/2007 | Shayani |
| 2007/0225791 A1 | 9/2007 | Molitor |
| 2007/0244502 A1 | 10/2007 | Deutsch |
| 2007/0250087 A1* | 10/2007 | Makower et al. ............. 606/157 |
| 2007/0250147 A1 | 10/2007 | Walther |
| 2007/0260179 A1 | 11/2007 | Sholev |
| 2007/0260268 A1 | 11/2007 | Bartee |
| 2007/0265710 A1 | 11/2007 | Brown |
| 2007/0270752 A1 | 11/2007 | LaBombard |
| 2007/0280990 A1 | 12/2007 | Stopek |
| 2007/0293717 A1 | 12/2007 | Kaleta |
| 2007/0293878 A1 | 12/2007 | Butsch |
| 2007/0299300 A1 | 12/2007 | Smith |
| 2007/0299542 A1 | 12/2007 | Mathisen |
| 2008/0015501 A1 | 1/2008 | Gertner |
| 2008/0021545 A1 | 1/2008 | Reneker |
| 2008/0033461 A1 | 2/2008 | Koeckerling |
| 2008/0035243 A1 | 2/2008 | Breitenkamp |
| 2008/0045952 A1 | 2/2008 | Kuslich |
| 2008/0065229 A1 | 3/2008 | Adams |
| 2008/0086216 A1 | 4/2008 | Wilson |
| 2008/0091222 A1 | 4/2008 | Deusch |
| 2008/0091276 A1 | 4/2008 | Deusch |
| 2008/0103351 A1 | 5/2008 | Montpetit |
| 2008/0113035 A1 | 5/2008 | Hunter |
| 2008/0125869 A1 | 5/2008 | Paz |
| 2008/0131509 A1 | 6/2008 | Hossainy |
| 2008/0132602 A1 | 6/2008 | Rizk |
| 2008/0147198 A1 | 6/2008 | Cherok |
| 2008/0147200 A1 | 6/2008 | Rousseau |
| 2008/0167519 A1 | 7/2008 | St-Germain |
| 2008/0167667 A1 | 7/2008 | Criscuolo |
| 2008/0167668 A1 | 7/2008 | Criscuolo |
| 2008/0188874 A1 | 8/2008 | Henderson |
| 2008/0193494 A1 | 8/2008 | Sabesan |
| 2008/0195121 A1 | 8/2008 | Eldar |
| 2008/0200979 A1 | 8/2008 | Dieck |
| 2008/0215154 A1 | 9/2008 | Lambrecht |
| 2008/0243149 A1 | 10/2008 | Kockerling |
| 2008/0255593 A1 | 10/2008 | St-Germain |
| 2008/0260794 A1 | 10/2008 | Lauritzen |
| 2008/0269896 A1 | 10/2008 | Cherok |
| 2008/0281433 A1 | 11/2008 | Chang |
| 2008/0287970 A1 | 11/2008 | Amato |
| 2008/0306497 A1 | 12/2008 | Brown |
| 2008/0312751 A1 | 12/2008 | Pugsley |
| 2009/0004239 A1 | 1/2009 | Ladet |
| 2009/0005867 A1 | 1/2009 | Lefranc |
| 2009/0012350 A1 | 1/2009 | Tihon |
| 2009/0012546 A1 | 1/2009 | N'diaye |
| 2009/0018559 A1 | 1/2009 | Buevich |
| 2009/0030434 A1 | 1/2009 | Paz |
| 2009/0030522 A1 | 1/2009 | Cauthen, III |
| 2009/0030527 A1 | 1/2009 | Richter |
| 2009/0036937 A1 | 2/2009 | Cauthen, III |
| 2009/0036989 A1 | 2/2009 | Cauthen, III |
| 2009/0036990 A1 | 2/2009 | Cauthen, III |
| 2009/0036996 A1 | 2/2009 | Roeber |
| 2009/0062823 A1 | 3/2009 | Richter |
| 2009/0069826 A1 | 3/2009 | Walther |
| 2009/0105526 A1 | 4/2009 | Piroli Torelli |
| 2009/0125041 A1 | 5/2009 | Dudai |
| 2009/0137864 A1 | 5/2009 | Cox |
| 2009/0149875 A1 | 6/2009 | Abele |
| 2009/0155332 A1 | 6/2009 | Sherry |
| 2009/0157184 A1 | 6/2009 | Cauthen, III |
| 2009/0157195 A1 | 6/2009 | Siedle |
| 2009/0162273 A1 | 6/2009 | Lawrynowicz |
| 2009/0182190 A1 | 7/2009 | Dann |
| 2009/0182352 A1 | 7/2009 | Paz |
| 2009/0187258 A1 | 7/2009 | Ip |
| 2009/0192346 A1 | 7/2009 | Rosenblatt |
| 2009/0192528 A1 | 7/2009 | Higgins |
| 2009/0198260 A1 | 8/2009 | Ford |
| 2009/0204130 A1 | 8/2009 | Kantsevoy |
| 2009/0204227 A1 | 8/2009 | Derwin |
| 2009/0216075 A1 | 8/2009 | Bell |
| 2009/0216104 A1 | 8/2009 | DeSimone |
| 2009/0216338 A1 | 8/2009 | Gingras |
| 2009/0234379 A1 | 9/2009 | Rehnke |
| 2009/0234461 A1 | 9/2009 | Rehnke |
| 2009/0240342 A1 | 9/2009 | Lindh |
| 2009/0240343 A1 | 9/2009 | Adams |
| 2009/0248048 A1 | 10/2009 | Milbocker |
| 2009/0254103 A1 | 10/2009 | Deutsch |
| 2009/0259094 A1 | 10/2009 | Bouchier |
| 2009/0281563 A1 | 11/2009 | Newell |
| 2010/0069930 A1 | 3/2010 | Roslin |
| 2010/0233021 A1* | 9/2010 | Sliwa et al. ..................... 422/20 |
| 2010/0312357 A1 | 12/2010 | Levin |
| 2010/0318121 A1 | 12/2010 | Levin |
| 2011/0004221 A1 | 1/2011 | Euteneuer |
| 2011/0040310 A1 | 2/2011 | Levin |
| 2011/0040311 A1 | 2/2011 | Levin |
| 2011/0054500 A1 | 3/2011 | Levin |
| 2011/0066166 A1* | 3/2011 | Levin et al. ................... 606/151 |
| 2011/0301701 A1 | 12/2011 | Padala |
| 2012/0046740 A1 | 2/2012 | Paul |
| 2012/0061448 A1* | 3/2012 | Zingman ............... A61B 17/072 227/175.2 |
| 2012/0259347 A1 | 10/2012 | Abuzaina |
| 2013/0018395 A1 | 1/2013 | Friedlander |
| 2013/0190784 A1 | 7/2013 | Palmer |
| 2013/0310637 A1* | 11/2013 | Iceman et al. .................. 600/37 |
| 2013/0310850 A1* | 11/2013 | Glick et al. .................... 606/142 |
| 2013/0310851 A1* | 11/2013 | Iceman et al. ................. 606/142 |
| 2013/0310852 A1* | 11/2013 | Bolduc et al. ................. 606/142 |
| 2013/0310857 A1* | 11/2013 | Iceman et al. ................. 606/151 |
| 2013/0310858 A1* | 11/2013 | Palmer et al. ................. 606/151 |

FOREIGN PATENT DOCUMENTS

| | | |
|---|---|---|
| EP | 0525791 | 2/1993 |
| EP | 0537769 | 4/1993 |
| EP | 0544485 | 6/1993 |
| EP | 0556018 | 8/1993 |
| EP | 0557963 | 9/1993 |
| EP | 0557964 | 9/1993 |
| EP | 0573273 | 12/1993 |
| EP | 0579377 | 1/1994 |
| EP | 0581036 | 2/1994 |
| EP | 0614650 | 9/1994 |
| EP | 0702934 | 3/1996 |
| EP | 0744162 | 11/1996 |
| EP | 0581036 | 1/1997 |
| EP | 0519022 | 12/1997 |
| EP | 0827724 | 3/1998 |
| EP | 0553344 | 9/1998 |
| EP | 0746258 | 9/1998 |
| EP | 0898944 | 3/1999 |
| EP | 0908482 | 4/1999 |
| EP | 0986993 | 3/2000 |
| EP | 0837660 | 5/2000 |
| EP | 1060714 | 12/2000 |
| EP | 1145693 | 10/2001 |
| EP | 1181899 | 2/2002 |
| EP | 1199037 | 4/2002 |
| EP | 1199038 | 4/2002 |
| EP | 1219265 | 7/2002 |
| EP | 0746267 | 11/2002 |
| EP | 1018980 | 1/2003 |
| EP | 1306061 | 5/2003 |
| EP | 1317904 | 6/2003 |
| EP | 1366717 | 12/2003 |
| EP | 0783270 | 6/2004 |
| EP | 1200010 | 3/2005 |
| EP | 1164967 | 5/2005 |
| EP | 1541183 | 6/2005 |
| EP | 0828453 | 11/2005 |
| EP | 1001717 | 11/2005 |
| EP | 1303230 | 11/2005 |
| EP | 1607048 | 12/2005 |

(56) References Cited

FOREIGN PATENT DOCUMENTS

| | | |
|---|---|---|
| EP | 1404250 | 2/2006 |
| EP | 1671604 | 6/2006 |
| EP | 1674048 | 6/2006 |
| EP | 1274473 | 7/2006 |
| EP | 0934024 | 8/2006 |
| EP | 1503683 | 8/2006 |
| EP | 1700579 | 9/2006 |
| EP | 1704832 | 9/2006 |
| EP | 1079741 | 11/2006 |
| EP | 0964645 | 7/2007 |
| EP | 1163019 | 10/2007 |
| EP | 1849440 | 10/2007 |
| EP | 1867348 | 12/2007 |
| EP | 1870056 | 12/2007 |
| EP | 1531739 | 2/2008 |
| EP | 1406557 | 11/2008 |
| EP | 1990014 | 11/2008 |
| EP | 2002800 | 12/2008 |
| EP | 1505927 | 1/2009 |
| EP | 1372525 | 3/2009 |
| EP | 1653880 | 4/2009 |
| EP | 2050474 | 4/2009 |
| EP | 1940312 | 7/2009 |
| FR | 2789888 | 8/2000 |
| WO | WO8204390 | 12/1982 |
| WO | WO92/06639 | 4/1992 |
| WO | WO9206639 | 4/1992 |
| WO | WO9211824 | 7/1992 |
| WO | WO9219162 | 11/1992 |
| WO | WO9221293 | 12/1992 |
| WO | WO9303685 | 3/1993 |
| WO | WO9309722 | 5/1993 |
| WO | WO9317635 | 9/1993 |
| WO | WO9417747 | 8/1994 |
| WO | WO9419029 | 9/1994 |
| WO | WO9427535 | 12/1994 |
| WO | WO9530374 | 11/1995 |
| WO | WO9531140 | 11/1995 |
| WO | WO9603091 | 2/1996 |
| WO | WO9603165 | 2/1996 |
| WO | WO9606634 | 3/1996 |
| WO | WO9609795 | 4/1996 |
| WO | WO9640307 | 12/1996 |
| WO | WO9702789 | 1/1997 |
| WO | WO9722371 | 6/1997 |
| WO | WO9732526 | 9/1997 |
| WO | WO9735533 | 10/1997 |
| WO | WO9803713 | 1/1998 |
| WO | WO9811814 | 3/1998 |
| WO | WO9814134 | 4/1998 |
| WO | WO9816153 | 4/1998 |
| WO | WO9903422 | 1/1999 |
| WO | WO9905992 | 2/1999 |
| WO | WO9916381 | 4/1999 |
| WO | WO9951163 | 10/1999 |
| WO | WO9960931 | 12/1999 |
| WO | WO9962406 | 12/1999 |
| WO | WO9963051 | 12/1999 |
| WO | WO0007520 | 2/2000 |
| WO | WO0016822 | 3/2000 |
| WO | WO0056376 | 9/2000 |
| WO | WO0057796 | 10/2000 |
| WO | WO0057812 | 10/2000 |
| WO | WO0061033 | 10/2000 |
| WO | WO0067663 | 11/2000 |
| WO | WO0071548 | 11/2000 |
| WO | WO0071549 | 11/2000 |
| WO | WO0108594 | 2/2001 |
| WO | WO0126588 | 4/2001 |
| WO | WO0154589 | 8/2001 |
| WO | WO0168653 | 9/2001 |
| WO | WO0170322 | 9/2001 |
| WO | WO0180788 | 11/2001 |
| WO | WO0185058 | 11/2001 |
| WO | WO0185060 | 11/2001 |
| WO | WO0189390 | 11/2001 |
| WO | WO0189392 | 11/2001 |
| WO | WO0207648 | 1/2002 |
| WO | WO0217771 | 3/2002 |
| WO | WO0217796 | 3/2002 |
| WO | WO0217797 | 3/2002 |
| WO | WO0219916 | 3/2002 |
| WO | WO0219923 | 3/2002 |
| WO | WO0222047 | 3/2002 |
| WO | WO0224080 | 3/2002 |
| WO | WO0226747 | 4/2002 |
| WO | WO0230336 | 4/2002 |
| WO | WO0232346 | 4/2002 |
| WO | WO0234140 | 5/2002 |
| WO | WO0235990 | 5/2002 |
| WO | WO02058543 | 8/2002 |
| WO | WO02078568 | 10/2002 |
| WO | WO02080779 | 10/2002 |
| WO | WO02080780 | 10/2002 |
| WO | WO02/091953 | 11/2002 |
| WO | WO02087425 | 11/2002 |
| WO | WO02091928 | 11/2002 |
| WO | WO02091953 | 11/2002 |
| WO | WO02096327 | 12/2002 |
| WO | WO03002029 | 1/2003 |
| WO | WO03002130 | 1/2003 |
| WO | WO03032867 | 4/2003 |
| WO | WO03059180 | 7/2003 |
| WO | WO03059201 | 7/2003 |
| WO | WO03059217 | 7/2003 |
| WO | WO03077730 | 9/2003 |
| WO | WO03082125 | 10/2003 |
| WO | WO03084410 | 10/2003 |
| WO | WO03088846 | 10/2003 |
| WO | WO03090633 | 11/2003 |
| WO | WO03092509 | 11/2003 |
| WO | WO03094781 | 11/2003 |
| WO | WO03094783 | 11/2003 |
| WO | WO03094786 | 11/2003 |
| WO | WO03094787 | 11/2003 |
| WO | WO03096909 | 11/2003 |
| WO | WO03096929 | 11/2003 |
| WO | WO03097011 | 11/2003 |
| WO | WO03099160 | 12/2003 |
| WO | WO03103473 | 12/2003 |
| WO | WO2004004600 | 1/2004 |
| WO | WO2004006808 | 1/2004 |
| WO | WO2004012579 | 2/2004 |
| WO | WO2004012627 | 2/2004 |
| WO | WO2004019787 | 3/2004 |
| WO | WO2004024030 | 3/2004 |
| WO | WO2004034924 | 4/2004 |
| WO | WO2004037123 | 5/2004 |
| WO | WO2004058286 | 7/2004 |
| WO | WO2004060425 | 7/2004 |
| WO | WO2004062529 | 7/2004 |
| WO | WO2004062530 | 7/2004 |
| WO | WO2004028547 | 8/2004 |
| WO | WO2004069866 | 8/2004 |
| WO | WO2004080348 | 9/2004 |
| WO | WO2004087227 | 10/2004 |
| WO | WO2004093737 | 11/2004 |
| WO | WO2004098461 | 11/2004 |
| WO | WO2004098665 | 11/2004 |
| WO | WO2004100841 | 11/2004 |
| WO | WO2004101002 | 11/2004 |
| WO | WO2004103166 | 12/2004 |
| WO | WO2004103414 | 12/2004 |
| WO | WO2005003351 | 1/2005 |
| WO | WO2005004727 | 1/2005 |
| WO | WO2005007209 | 1/2005 |
| WO | WO2005014634 | 2/2005 |
| WO | WO2005018494 | 3/2005 |
| WO | WO2005019241 | 3/2005 |
| WO | WO2005019315 | 3/2005 |
| WO | WO2005035548 | 4/2005 |
| WO | WO2005041784 | 5/2005 |
| WO | WO2005044143 | 5/2005 |
| WO | WO2005051172 | 6/2005 |

(56) References Cited

FOREIGN PATENT DOCUMENTS

| | | |
|---|---|---|
| WO | WO2005055958 | 6/2005 |
| WO | WO2005065324 | 7/2005 |
| WO | WO2005065552 | 7/2005 |
| WO | WO2005079335 | 9/2005 |
| WO | WO2005082273 | 9/2005 |
| WO | WO2005082274 | 9/2005 |
| WO | WO2005094721 | 10/2005 |
| WO | WO2005099628 | 10/2005 |
| WO | WO2005102209 | 11/2005 |
| WO | WO2005105172 | 11/2005 |
| WO | WO2005110243 | 11/2005 |
| WO | WO2005110273 | 11/2005 |
| WO | WO2006002439 | 1/2006 |
| WO | WO2006008429 | 1/2006 |
| WO | WO2006012353 | 2/2006 |
| WO | WO2006013337 | 2/2006 |
| WO | WO2006015031 | 2/2006 |
| WO | WO2006026509 | 3/2006 |
| WO | WO2006034117 | 3/2006 |
| WO | WO2006036936 | 4/2006 |
| WO | WO2006037047 | 4/2006 |
| WO | WO2006040760 | 4/2006 |
| WO | WO2006044785 | 4/2006 |
| WO | WO2006047645 | 5/2006 |
| WO | WO2006048885 | 5/2006 |
| WO | WO2006/082587 | 8/2006 |
| WO | WO2006082587 | 8/2006 |
| WO | WO2006086339 | 8/2006 |
| WO | WO2006092159 | 9/2006 |
| WO | WO2006092236 | 9/2006 |
| WO | WO2006102457 | 9/2006 |
| WO | WO200614650 | 10/2006 |
| WO | WO2006116000 | 11/2006 |
| WO | WO2006119034 | 11/2006 |
| WO | WO2007004228 | 1/2007 |
| WO | WO2007011689 | 1/2007 |
| WO | WO2007017872 | 2/2007 |
| WO | WO2007021620 | 2/2007 |
| WO | WO2007021759 | 2/2007 |
| WO | WO2007021834 | 2/2007 |
| WO | WO2007025293 | 3/2007 |
| WO | WO2007025296 | 3/2007 |
| WO | WO2007025302 | 3/2007 |
| WO | WO2007030676 | 3/2007 |
| WO | WO2007034145 | 3/2007 |
| WO | WO2007050382 | 5/2007 |
| WO | WO2007051221 | 5/2007 |
| WO | WO2007055755 | 5/2007 |
| WO | WO2007070141 | 6/2007 |
| WO | WO2007072469 | 6/2007 |
| WO | WO2007081955 | 7/2007 |
| WO | WO2007087132 | 8/2007 |
| WO | WO2007087146 | 8/2007 |
| WO | WO2007115110 | 10/2007 |
| WO | WO2007129220 | 11/2007 |
| WO | WO2007133311 | 11/2007 |
| WO | WO2007136820 | 11/2007 |
| WO | WO2007137211 | 11/2007 |
| WO | WO2007143726 | 12/2007 |
| WO | WO2007144782 | 12/2007 |
| WO | WO2007146784 | 12/2007 |
| WO | WO2008006097 | 1/2008 |
| WO | WO2008016802 | 2/2008 |
| WO | WO2008026905 | 3/2008 |
| WO | WO2008030873 | 3/2008 |
| WO | WO2008030939 | 3/2008 |
| WO | WO2008045635 | 4/2008 |
| WO | WO2008055028 | 5/2008 |
| WO | WO2008065653 | 6/2008 |
| WO | WO2008069919 | 6/2008 |
| WO | WO2008083484 | 7/2008 |
| WO | WO2008085825 | 7/2008 |
| WO | WO2008094217 | 8/2008 |
| WO | WO2008094842 | 8/2008 |
| WO | WO2008099382 | 8/2008 |
| WO | WO2008112437 | 9/2008 |
| WO | WO2008124056 | 10/2008 |
| WO | WO2008140989 | 11/2008 |
| WO | WO2008157497 | 12/2008 |
| WO | WO2008157777 | 12/2008 |
| WO | WO2009005625 | 1/2009 |
| WO | WO2009005634 | 1/2009 |
| WO | WO2009011824 | 1/2009 |
| WO | WO2009012001 | 1/2009 |
| WO | WO2009022348 | 2/2009 |
| WO | WO2009036094 | 3/2009 |
| WO | WO2009039371 | 3/2009 |
| WO | WO2009/050717 | 4/2009 |
| WO | WO2009042442 | 4/2009 |
| WO | WO2009048314 | 4/2009 |
| WO | WO2009050717 | 4/2009 |
| WO | WO2009059005 | 5/2009 |
| WO | WO2009064845 | 5/2009 |
| WO | WO2009069119 | 6/2009 |
| WO | WO2009075786 | 6/2009 |
| WO | WO2009075932 | 6/2009 |
| WO | WO2009075933 | 6/2009 |
| WO | WO2009086446 | 7/2009 |
| WO | WO2009092294 | 7/2009 |
| WO | WO2009094015 | 7/2009 |
| WO | WO2009097380 | 8/2009 |
| WO | WO2009102792 | 8/2009 |
| WO | WO2009104182 | 8/2009 |
| WO | WO2009113972 | 9/2009 |
| WO | WO2009126781 | 10/2009 |
| WO | WO2011021082 | 2/2011 |
| WO | WO2012112565 | 8/2012 |

OTHER PUBLICATIONS

European Search Report corresponding to EP 11 25 0797.5, completed Jun. 12, 2012; (9 pp).
Extended European Search Report corresponding to EP 13 16 4453.6, completed Jul. 29, 2013 and mailed Aug. 5, 2013; (7 pp).
Extended European Search Report corresponding to EP 13 18 1255.4, completed Nov. 12, 2013 and mailed Nov. 22, 2013; (6 pp).
Extended European Search Report corresponding to EP 13 18 1220.8, completed Nov. 12, 2013 and mailed Nov. 27, 2013; (8 pp).
Extended European Search Report corresponding to EP 13 18 1217, completed Nov. 14, 2013 and mailed Nov. 27, 2013; (8 pp).
EP Examination Report dated Mar. 26, 2015 from Application No. EP 13181252.1.

* cited by examiner

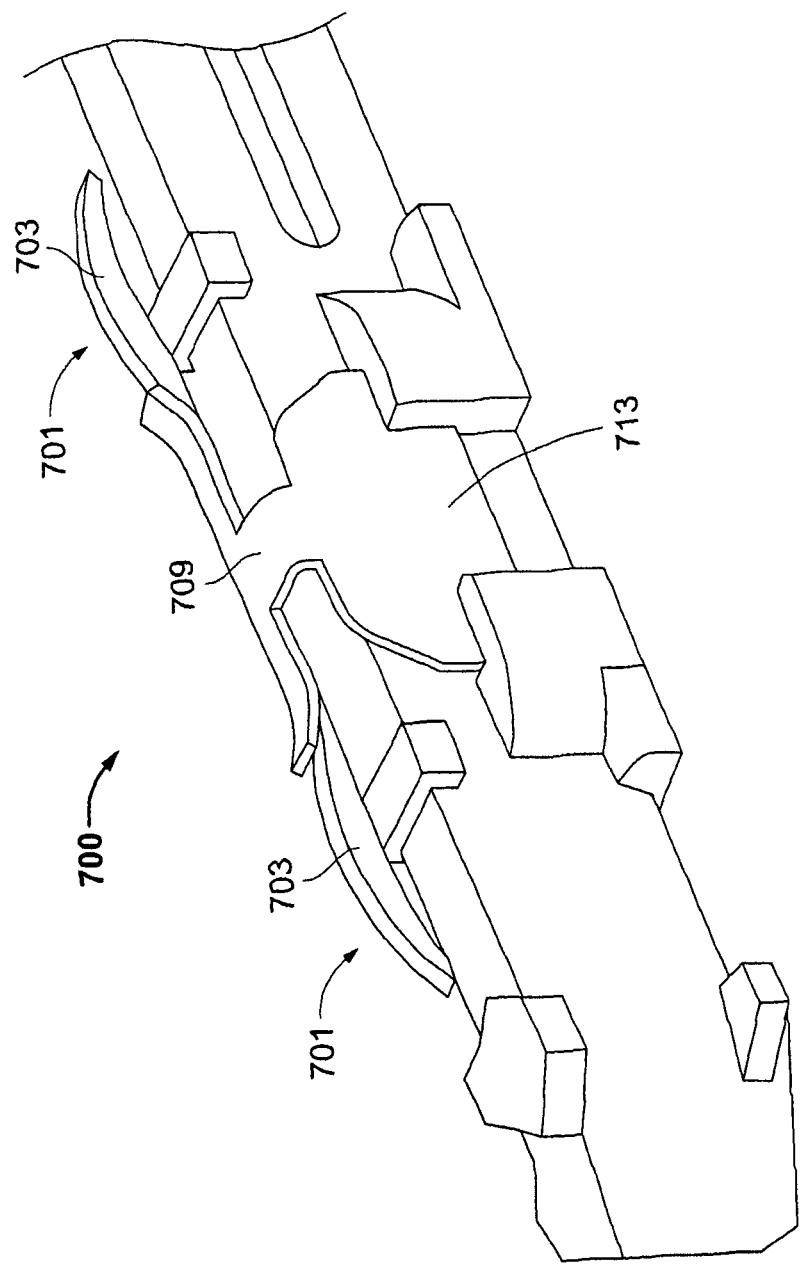

CLIP FOR IMPLANT DEPLOYMENT DEVICE

CROSS-REFERENCE TO RELATED APPLICATIONS

The present application is a continuation-in-part of U.S. patent application Ser. No. 13/451,962, filed on Apr. 20, 2012, now U.S. Pat. No. 8,753,361, which is a continuation-in-part of U.S. patent application Ser. No. 12/891,962, filed on Sep. 28, 2010, now U.S. Pat. No. 8,758,373, which is a continuation-in-part of U.S. patent application Ser. No. 12/834,456, filed Jul. 12, 2010, now U.S. Pat. No. 8,753,359, which is a continuation-in-part of PCT international patent application number PCT/IL2009/000188, filed Feb. 18, 2009, which claims the benefit of and priority to U.S. provisional patent application Ser. No. 61/029,386, filed Feb. 18, 2008. The present application also claims the benefit of and priority to U.S. provisional patent application Ser. No. 61/691,859, filed Aug. 22, 2012, which claims the benefit of and priority to U.S. provisional patent application Ser. No. 61/691,860, filed Aug. 22, 2012, which claims the benefit of and priority to U.S. provisional patent application Ser. No. 61/691,863, filed Aug. 22, 2012, which claims the benefit of and priority to U.S. provisional patent application Ser. No. 61/691,864, filed Aug. 22, 2012, which claims the benefit of and priority to U.S. provisional patent application Ser. No. 61/691,866, filed Aug. 22, 2012, which claims the benefit of and priority to U.S. provisional patent application Ser. No. 61/691,869, filed Aug. 22, 2012. The present application also claims the benefit of and priority to U.S. provisional patent application Ser. No. 61/302,186, filed Feb. 8, 2010. The contents of each of these prior applications are incorporated by reference herein in their entirety.

FIELD OF THE INVENTION

This invention generally relates to a device and method for reversibly coupling an implant to an implant deployment device.

BACKGROUND

An object of the present invention is to provide an apparatus and a method for performing corrective surgery on internal wounds such as a hernia where invasion of the patient's body tissues is minimized and resultant trauma is reduced.

A hernia is a protrusion of a tissue, structure, or part of an organ through the muscular tissue or the membrane by which it is normally contained. In other words, a hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery, patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques, several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the implant and then attach the implant to the tissue.

There are many patents and patent applications relating to attaching a prosthesis implant to a tissue via tacks. Each patent and patent application describes a different attachment mechanism via different anchoring means (see for example U.S. Pat. No. 6,447,524). Traditional anchors used in surgery include clips, staples, or sutures, and may also be referred to as tissue anchors. These devices are usually made of a biocompatible material (or are coated with a biocompatible material), so that they can be safely implanted into the body.

Most tissue anchors secure the tissue by impaling it with one or more posts or legs that are bent or crimped to lock the tissue into position. Thus, most traditional anchors are rigid or are inflexibly attached to the tissue. For example PCT No. WO 07/021834 describes an anchor having two curved legs that cross in a single turning direction to form a loop. Those two curved legs are adapted to penetrate tissue in a curved pathway. U.S. Pat. No. 4,485,816 describes surgical staple made of shape memory alloy. The staple is placed in contact of the tissue and then heated. The heating causes the staple to change its shape thus, penetrating the tissue.

U.S. Pat. No. 6,893,452 describes a tissue attachment device that facilitates wound healing by holding soft tissue together under improved distribution of tension and with minimal disruption of the wound interface and its nutrient supplies.

U.S. Pat. No. 6,517,584 describes a hernia implant which includes at least one anchoring device made of shape memory material. The anchoring devices are initially secured to the prosthesis by being interlaced through a web mesh constituting the prosthesis. The attachment is obtained by altering the attachment element's shape from rectilinear to a loop shape due to heat induced shape memory effect.

Yet other patent literature relates to devices for endoscopic application of surgical staples adapted to attach surgical mesh to a body tissue.

An example of such a teaching is to be found in U.S. Pat. No. 5,364,004; U.S. Pat. No. 5,662,662; U.S. Pat. No. 5,634,584; U.S. Pat. No. 5,560,224; U.S. Pat. No. 5,588,581; and in U.S. Pat. No. 5,626,587.

There are a few patent and patent applications teaching the deployment of implants. For example U.S. Pat. No. 5,836,961 which relates to an apparatus used for developing an anatomic space for laparoscopic hernia repair and an implant for use therewith. The apparatus of U.S. Pat. No. 5,836,961 comprises a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

More patent literature can be found in PCT No. WO 08/065653 which relates to a device especially adapted to deploy an implant within a body cavity. The device is an elongate open-bored applicator and comprises (a) at least one inflatable contour-balloon, (b) at least one inflatable dissection balloon. The inflatable contour-balloon and the inflatable dissection balloon are adjustable and located at the distal portion. The elongate open-bored applicator additionally comprises (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

Although all the above described patents and patent applications demonstrate attachment means or deployment means, none of the literature found relates to a reversible connection device which enable a reversible coupling between the implant and the implant deployment device.

Thus, there is still a long felt need for a device that will enable a reversible connection between the implant and the implant deployment device.

SUMMARY

It is one object of the present invention to provide an active reversible connection mechanism adapted to provide a reversible attachment between a prosthetic implant and an implant deployment device, wherein said attachment can be actively reversed without requiring any application of force on said implant.

It is another object of the present invention to provide the active reversible connection mechanism as defined above, wherein said active reversible connection mechanism comprising at least one clip, hinge-like coupled to said implant deployment device, adapted to attach said implant to said implant deployment device: Said clip is characterized by having at least three configurations: (i) a horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate; such that (i) when said clip is in said horizontal configuration said attachment between said implant and said implant deployment device is obtained; (ii) when said clip is in said free motion configuration said detachment between said implant and said implant deployment device is obtained.

It is another object of the present invention to provide the active reversible connection mechanism as defined above, additionally comprising at least one locking bar characterized by at least two configurations: (i) lock configuration in which said lock bar maintains said clip in said horizontal configuration; and, (ii) free configuration in which said locking bar enables said clip a free movement.

It is another object of the present invention to provide the active reversible connection mechanism as defined above, wherein said active reversible connection additionally comprising at least one detachment actuator adapted to reversibly transform said locking bar from said lock configuration to said free configuration.

It is another object of the present invention to provide the active reversible connection mechanism as defined above, wherein said attachment between said implant and said implant deployment device is obtained once said locking bar is in its said lock configuration and said at least one clip is in said horizontal configuration such that the same at least partially penetrates said implant.

It is another object of the present invention to provide the active reversible connection mechanism as defined above, wherein said detachment is achieved by transforming said locking bar from said lock configuration to said free configuration via said at least one detachment actuator.

It is another object of the present invention to provide the active reversible connection mechanism as defined above, wherein said detachment actuator comprises a wire; further wherein said wire is attached to said lock bar.

It is another object of the present invention to provide the active reversible connection mechanism as defined above, wherein said transformation of said clip from said vertical configuration into their said horizontal configuration is performed manually by the physician or by the aid of a dedicated device.

It is another object of the present invention to provide a method for attaching a prosthetic implant to an implant deployment device. The method comprising steps selected, inter alia, from:

a. obtaining an active reversible connection mechanism adapted to provide a reversible attachment between said prosthetic implant and said implant deployment device; wherein said attachment can be actively reversed without requiring any application of force on said implant; said active reversible connection comprising i. at least one clip, hinge-like coupled to said implant deployment device, adapted to attach said implant to said implant deployment device: Said clip is characterized by having at least three configurations: (i) horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate;

ii. at least one locking bar characterized by at least two configurations: (i) lock configuration in which said lock bar maintains said clip in said horizontal configuration; and, (ii) free configuration in which said locking bar enables said clip a free movement; and, b. providing said clips in said vertical configuration;

c. providing said locking bar in said lock configuration;

d. threading said implant through said clip;

e. transforming said clip into its said horizontal configuration thereby providing said attachment between said implant and said implant deployment device;

It is another object of the present invention to provide the method as defined above, additionally comprising the step of providing said active reversible connection with at least one detachment actuator.

It is another object of the present invention to provide the method as defined above, additionally comprising the step of reversibly transforming said locking bar from said lock configuration to said free configuration via said detachment actuator; thereby enabling free rotation of said clip such that detachment between said implant and said implant deployment device is obtained.

It is another object of the present invention to provide the method as defined above, additionally comprising the step of introducing said implant deployment device into a body cavity.

It is another object of the present invention to provide the method as defined above, additionally comprising the step of detaching said implant from said implant deployment device.

It is another object of the present invention to provide the method as defined above, wherein said detachment additionally comprising the steps of reversibly transforming said locking bar from said lock configuration to said free configuration via said detachment actuator; thereby enabling said clip to rotate freely such that said detachment between said implant and said implant deployment device is obtained.

It is another object of the present invention to provide a hernia kit useful in minimal invasive hernia surgery, comprising:

a. an implant;
 b. an implant deployment device, adapted to deploy said implant within the abdominal cavity; and,
 c. an active reversible connection mechanism for reversible attaching said implant to said implant deployment device;

wherein attachment can be actively reversed without requiring any application of force on said implant.

It is another object of the present invention to provide the hernia kit as defined above, wherein said active reversible connection mechanism comprising:

a. at least one clip, hinge-like coupled to said implant deployment device, adapted to attach said implant to said implant deployment device: Said clip is characterized by having at least three configurations: (i) horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate; such that (i) when said clip is in said horizontal configuration said attachment between said implant and said implant deployment device is obtained; (ii) when said clip is in said free motion configuration said detachment between said implant and said implant deployment device is obtained.

It is another object of the present invention to provide the hernia kit as defined above, additionally comprising at least one locking bar characterized by at least two configurations: (i) lock configuration in which said lock bar maintains said clip in said horizontal configuration; and, (ii) free configuration in which said locking bar enables said clip a free movement.

It is another object of the present invention to provide the hernia kit as defined above, wherein said active reversible connection additionally comprising at least one detachment actuator adapted to reversibly transform said locking bar from said lock configuration to said free configuration.

It is another object of the present invention to provide the hernia kit as defined above, wherein said attachment between said implant and said implant deployment device is obtained once said locking bar is in its said lock configuration and said at least one clip is in said horizontal configuration such that the same at least partially penetrates said implant.

It is another object of the present invention to provide the hernia kit as defined above, wherein said detachment is achieved by transforming said locking bar from said lock configuration to said free configuration via said at least one detachment actuator.

It is still an object of the present invention to provide the hernia kit as defined above, wherein said detachment actuator comprises a wire; further wherein said wire is attached to said lock bar.

It is an object of the present invention to provide the hernia kit as defined above, wherein said transformation of said clip from said vertical configuration into their said horizontal configuration is performed manually by the physician or by the aid of a dedicated device.

At least one aspect of this disclosure includes a system for closing an aperture in a biological tissue, the system including a proximal portion adapted to remain outside the body, a distal portion adapted to be inserted into the body, the distal portion including at least one frame arm, and at least one clip spring system connected to the at least one frame arm and configured to releasably retain a surgical implant, wherein each clip spring system includes two clips and at least one spring member attached to each clip, wherein the at least one clip spring system biases the clips towards a closed position.

In at least one aspect of this disclosure, the at least one clip further includes a hook, wherein at least one spring member is connected to the hook.

In at least one aspect of this disclosure, the at least one clip further includes a body portion, wherein the at least one spring member is connected to the body.

In at least one aspect of this disclosure, each clip further includes a locking tab, wherein the at least one spring member is connected to the locking tab.

In at least one aspect of this disclosure, the at least one spring member is removably attached to at least one of the clips.

In at least one aspect of this disclosure, the at least one spring member includes one or more of a coiled linear spring.

In at least one aspect of this disclosure, the at least one spring member includes one or more of a coiled torsion spring.

In at least one aspect of this disclosure, the at least one spring member includes one or more of a bendable member including at least one arm attached to at least one of the clips and an anchor portion fixed to the frame arm, wherein the arm is configured to bend and provide a restoring force against at least one of the clips when at least one of the clips is in an open position.

In at least one aspect of this disclosure, the one or more bendable member includes a V-shaped member.

In at least one aspect of this disclosure, the V-shaped members are formed from a single piece of metal rod.

In at least one aspect of this disclosure, the one or more bendable members includes a W-shaped member.

In at least one aspect of this disclosure, the W-shaped member is formed from a single piece of metal rod.

In at least one aspect of this disclosure, a clip system for releasably retaining a mesh to an implant deployment device includes at least one clip spring system connectable to the implant deployment device and configured to releasably retain a surgical implant, wherein each clip spring system includes two clips and at least one spring member attached to each clip.

In at least one aspect of this disclosure, the at least one clip further includes a hook, wherein at least one spring member is connected to the hook.

In at least one aspect of this disclosure, the at least one clip further includes a body portion, wherein the at least one spring member is connected to the body portion.

In at least one aspect of this disclosure, each clip further includes a locking tab, wherein the at least one spring member is connected to the locking tab.

In at least one aspect of this disclosure, the at least one spring member includes at least one coiled linear spring.

In at least one aspect of this disclosure, the at least one spring member includes at least one coiled torsion spring.

In at least one aspect of this disclosure, the at least one spring member includes one or more of a bendable member including at least one arm attached to at least one of the clips and an anchor portion fixed to the frame arm, wherein the arm is configured to bend and provide a restoring force against at least one of the clips when the at least one clip is in an open position.

In at least one aspect of this disclosure, the bendable member includes a V-shaped member.

In at least one aspect of this disclosure, the V-shaped member is formed from a single piece of metal rod.

In at least one aspect of this disclosure, the one or more bendable member includes a W-shaped member.

In at least one aspect of this disclosure, the W-shaped member is formed from a single piece of metal rod.

BRIEF DESCRIPTION OF THE DRAWINGS

The invention is herein described, by way of example only, with reference to the accompanying drawings, wherein:

FIG. 7C is a perspective view of the embodiment of FIGS. 7A and 7B in a closed position;

DETAIL DESCRIPTION OF THE SPECIFIC EMBODIMENTS

Figure 1A:
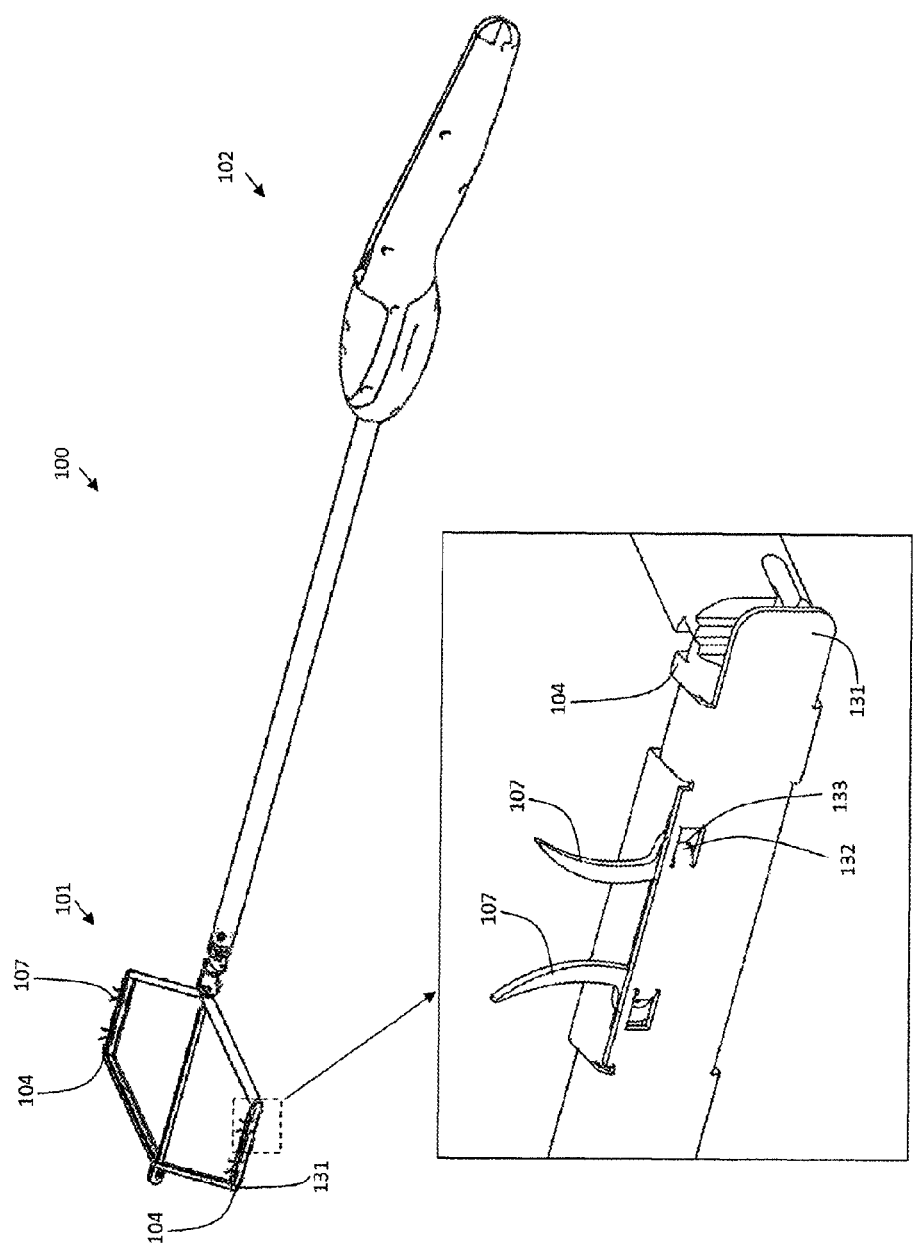
FIG. 1A illustrates an example of a implant deployment device which comprises said active reversible connection mechanism.

The following description is provided, alongside all chapters of the present invention, so as to enable any person skilled in the art to make use of the invention and sets forth the best modes contemplated by the inventor of carrying out this invention. Various modifications of the present disclosure should be apparent to those skilled in the art, since the generic principles of the present invention have been defined specifically to provide means and method for creating a reversible and active connection between an implant and an implant deployment device.

The present invention provides an active reversible connection mechanism between a prosthetic implant and an implant deployment device wherein said connection can be performed during a surgery at a standard surgery room by the medical staff.

Furthermore, the present invention provides means so as to enable the surgeon to actively eliminate said attachment once detachment between said implant deployment device and said implant is necessary.

It should be emphasized that some of the major advantages of the present invention, with respect to the prior art, is to provide a fast and intuitive method for creating a reliable connection between an implant and an implant deployment device in the surgery room. Embodiments of an implant include, but are not limited to, a surgical patch, a surgical mesh, or other biocompatible implants usable in repairing a defect in body tissue.

In addition, the present invention provides means to actively disconnect said implant from said implant deployment device, when said disconnection is desired without the need to exert large forces on said implant and/or said tissue.

The term "Hernia" refers hereinafter for umbilical hernia, hiatal hernia, ventral hernia, postoperative hernia, epigastric hernia, spiegelian hernia, inguinal hernia and femoral hernia, generally any abdominal wall related hernia.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components.

The term "hinge like connection" can refer to a standard hinge or to a living hinge (i.e., a thin flexible hinge (flexure bearing) made from plastic that joins two rigid parts together while allowing them to bend along the line of the hinge).

The term "controlled deployment" refers hereinafter to an implant deployment which is continuous. Thus, deployment using the presently disclosed implant deployment device is variable amongst a number of deployment levels between a fully opened position and a fully closed position rather than a binary arrangement that does not include any intermediate positions or levels between fully opened and fully closed. This is in contrast to some conventional deployment systems in which the deployment of the implant relies upon the elasticity of a loop member surrounding the implant such that the implant can be either fully folded or fully unfolded. No intermediate stages are enabled. In the present invention, there can be several deployment stages.

The term "bidirectional" or "fully reversible deployment" refers hereinafter to the deployment of the implant, which according to the present invention, is fully reversible. In other words, the implant deployment is bidirectional, i.e., the implant can be fully folded (i.e., deployed within the body) and then, if the surgeon desires, the implant can be fully unfolded simply by the reconfiguration of the flexible arms from the initial stage to the final stage and vice versa.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "articulation" refers hereinafter to a joint or juncture between two segments of the device. The articulating means of the present invention provides the ability to better adjust the device to the curvature of the treated tissue.

The term "orientation" refers hereinafter to the rotation of the mesh within the abdominal cavity so as to fit to the hernia. Usually the mesh is not symmetric in shape (e.g. rectangular or elliptical)—therefore it has different directions. By rotating the mesh within the abdominal cavity—one can decide which direction is turned where.

The term "adjusting" refers hereinafter to rolling, folding, and winding of the implant, thus preparing and enabling the insertion of said implant into the abdominal cavity.

The term "active reversible connection" refers hereinafter to a coupling between the implant and the implant deployment device implant deployment device in which the coupling/decoupling between the implant and the implant deployment device is enabled by an act performed by the user (namely the physician). Once said user performed said act, said coupling/decoupling is canceled.

According to the present invention the coupling/decoupling is obtained actively via the aid of dedicated clips which are characterized by at least two configurations:

(a) substantially horizontal/parallel configuration (in which an attachment between the implant and the implant deployment device is provided);

(b) substantially vertical configuration; and, (c) a configuration in which the clips are free to rotate.

Before explaining the figures, it should be understood that the invention is not limited in its application to the details of construction and the arrangement of the components set forth in the following description or illustrated in the drawings. The invention can be carried out in various ways.

Reference is now being made to FIG. 1A illustrates an example of an implant deployment device 100 which comprises said active reversible connection mechanism.

Implant deployment device 100 is defined hereinafter as a surgical device which can introduce an implant into a body cavity of a patient; implant deployment device 100 can deploy said implant such that it is at least partially spared inside the body cavity; alternatively implant deployment device 100 can only introduce said implant into the body cavity without performing any deployment.

In general, implant deployment device 100 comprises at least two portions: a distal portion 101 and a proximal portion 102. The proximal portion is adapted to remain outside the body, adjacently to the user and the distal portion 101 is adapted to be inserted into the body.

The distal portion comprises at least one frame arm 104 to which the implant is attached. Each frame arm 104 comprises said active reversible connection mechanism which provides reversible attachment between each frame arm 104 and the implant 106 such that said implant can be rolled/folded on said distal portion 101, and inserted into the patient's body cavity through a laparoscopic cannula or a small incision.

It should be noted that the term reversible refers hereinafter to the ability to both attach the implant to the implant deployment device and to decouple the same from the implant deployment device.

Said active reversible connection mechanism comprises at least one clip 107. Said clip is coupled to said frame arm 104 by hinge tab 132. Said active reversible connection is covered by cover 131 which is attached to the frame arm 104. Cover 131 comprises at least one hinge tab 132 which is adapted to hold said clip 107 attached to frame arm 104 an to serve as a hinge allowing free rotation of said clip 107. Said hinge tab 132 is inserted through hinge hole 133, located at clip 107 and through hole 134, located at frame arm 104.

Reference is now being made to FIGS. 2A-2D which illustrate the internal operation of said active reversible connection mechanism. For the purpose of illustration only, cover 131 is removed from these drawings.

A locking bar 203 is located inside groove 204 at frame arm 104. Said locking bar 203 can move linearly inside said groove 204 and comprises at least one groove 205. Said locking bar 203 is characterized by at least two positions: free position, in which each of said groove/s 205 is substantially located below said clip 107 (see FIGS. 2C and 2D), and lock position, in which said groove 205 is located away from said clip 107 (see FIGS. 2A and 2B).

In the lock position of the locking bar 203, the clip 107 are substantially perpendicular to the frame arm 104; and in free position of the locking bar 203, the clip 107 are free to rotate (hence, as will be discussed hereinafter a detachment is enabled).

A disconnection wire 206 is attached to said locking bar 203. Said wire 206 can be pulled proximally to the proximal portion 102 and is adapted to transform said locking bar 203 from its said lock position into its said free position.

According to this embodiment, each clip 107 comprises at least 3 sections: protruding portion (PP) 201 adapted to protrude through said implant during said connection process, hinge hole 133, and locking tab 202 which is tilted toward frame arm 104.

Figure 2A:
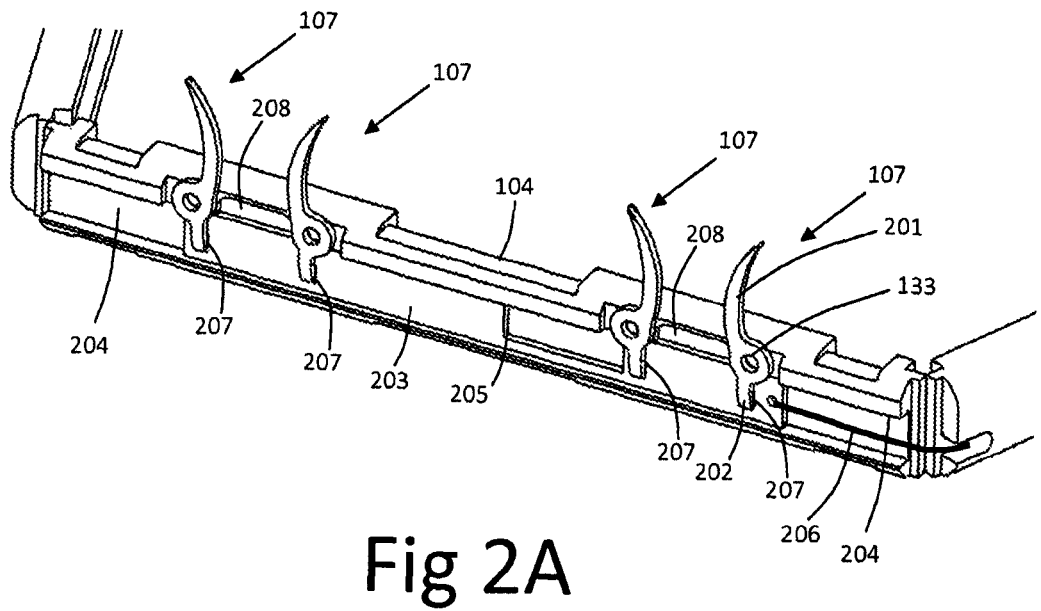
FIGS. 2A-2D illustrate the internal operation of said active reversible connection mechanism.
Figure 2B:
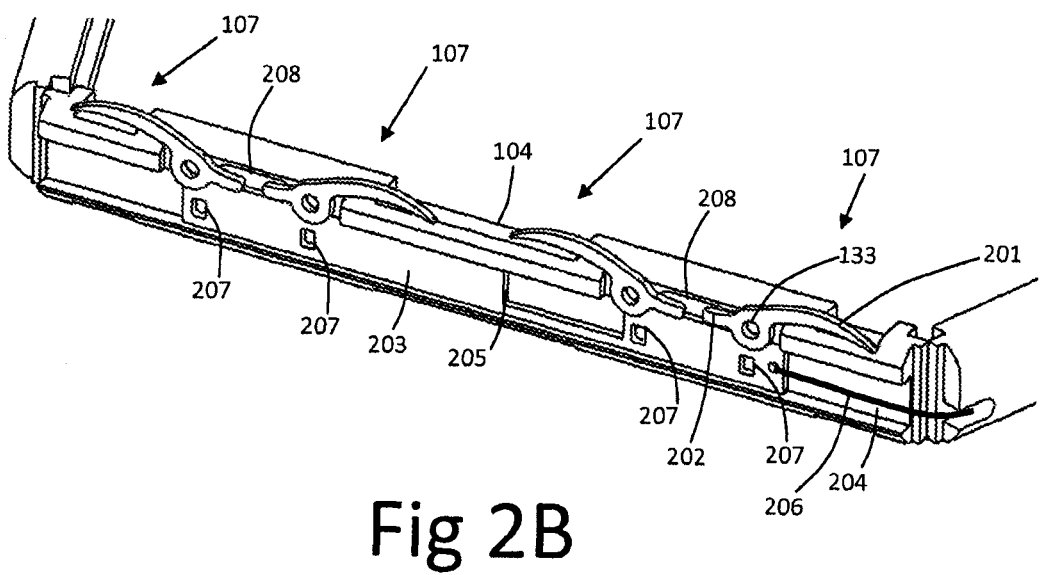
Figure 2C:
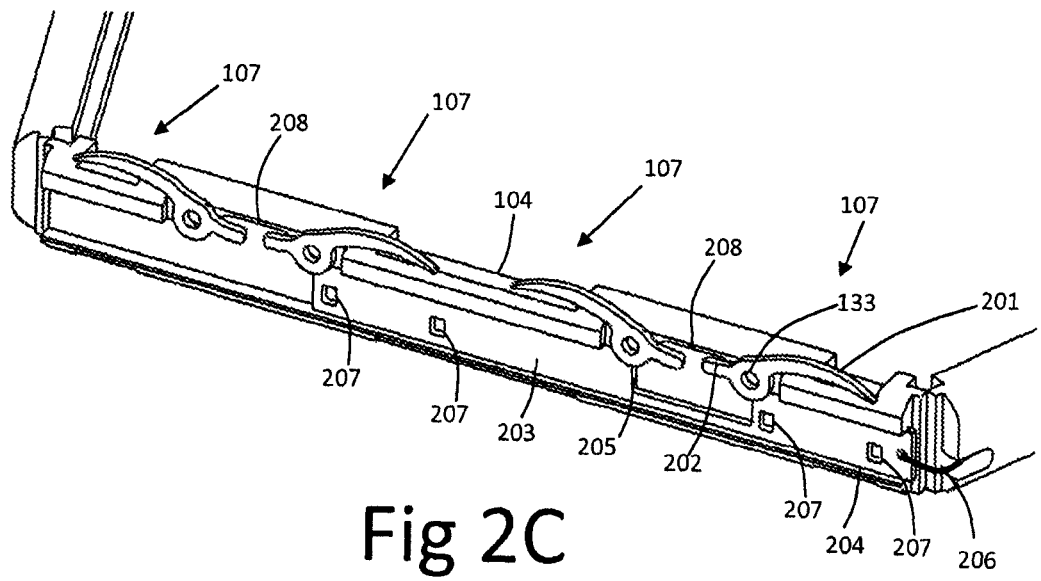
Figure 2D:
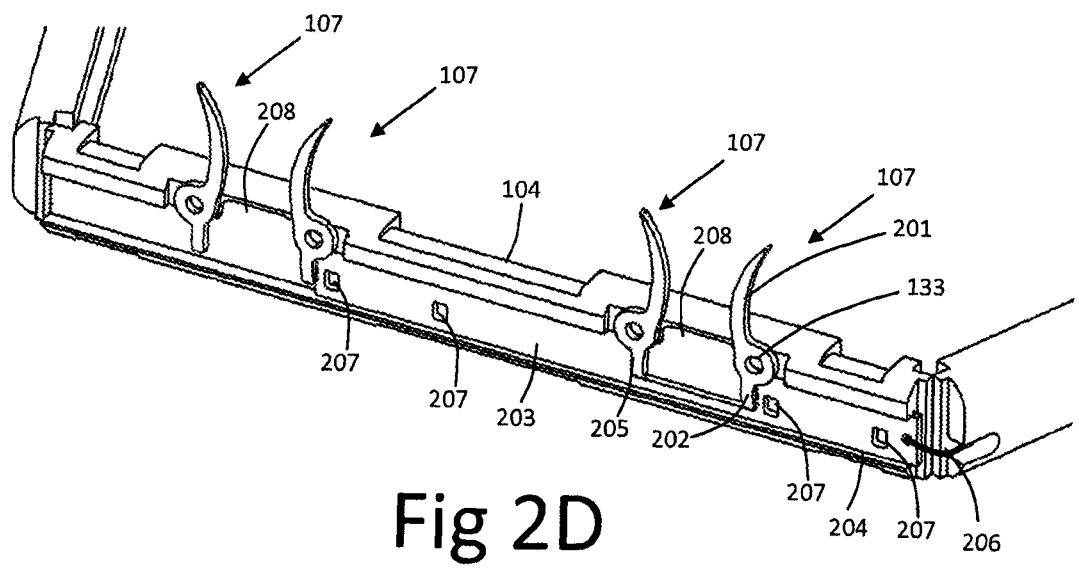

Each of said clip 107 is characterized by at least two configurations: horizontal/parallel configuration in which said clip 107 is substantially horizontal and parallel to said frame arm 104 (FIGS. 2B, 2C) and vertical configuration in which said clip 107 is substantially vertical with respect to said frame arm 104 (FIGS. 2A and 2D).

At least one holding hole 207 is located at said locking bar 203 and is adapted to hold said clip 107 in its vertical configuration.

At least one niche 208 in located at frame arm 104 adapted to accommodate said locking tab 202 of said clip 107 while the clip 107 is in its said horizontal/parallel configuration.

Reference is now being made to FIGS. 3A-3D illustrating a method of using said active reversible connection mechanism in order to provide said reversible connection between said implant and said implant deployment device 100. Again, for the purpose of illustration only, cover 131 was removed from these drawings.

Figure 3A:
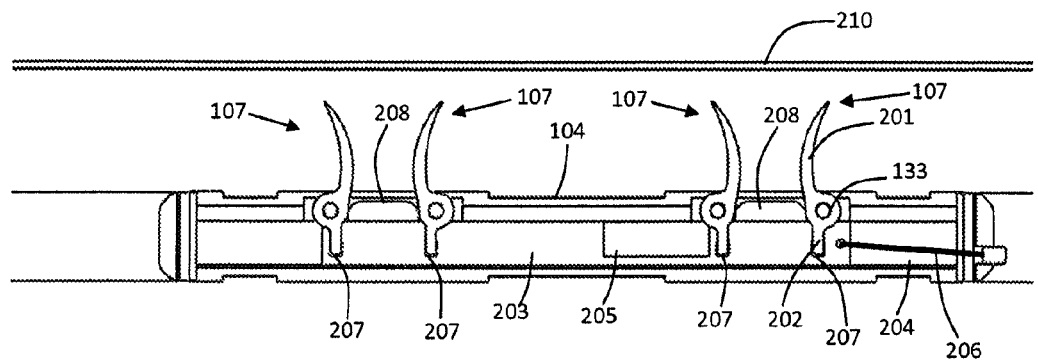
FIGS. 3A-3E illustrate a method of using said active reversible connection mechanism for providing said reversible connection between said implant and said implant deployment device.

FIG. 3A illustrates the initial state of said active reversible connection mechanism in which all of said clip 107 are in their vertical configuration and said locking bar 203 is positioned in said lock position.

Figure 3B:
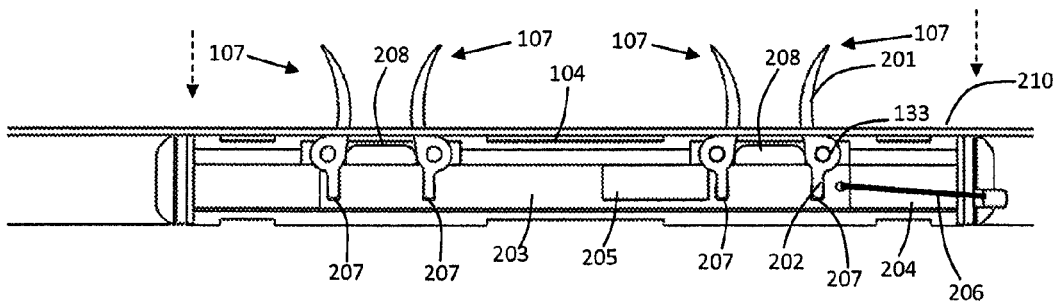

As can be seen in the figure, said locking tab 202 of each said clip 107 is located inside said holding hole 207, therefore each clip 107 is held in its said vertical configuration and can penetrate an implant 210 whilst the last is mounted on top of said implant deployment device (see FIG. 3B).

Figure 3C:
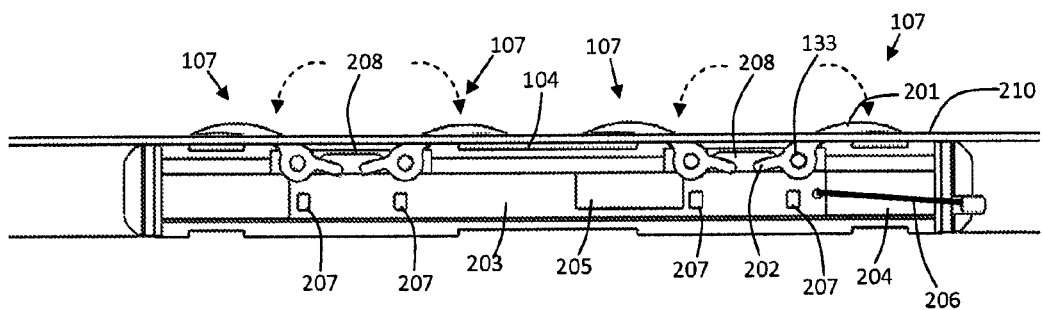

Once said implant is mounted, each of said clip 107 is transformed from said vertical configuration into their said horizontal configuration (see FIG. 3C).

Said transformation can be achieved either manually (i.e., the physician will manually rotate the clips 107 thereby transforming them from said vertical configuration into their said horizontal configuration) or by the aid of a dedicated device.

Once said clip 107 is transformed to its horizontal configuration while said locking bar is in its said lock position, said locking tab 202 is urged into niche 208. Since the locking tab 202 is titled inwardly, if said clip 107 is pulled upwardly in this state, the locking tab 202 is stopped by the upper edge of said locking bar 203, therefore, the rotation back to said vertical configuration of said clip 107 is limited by said locking bar 203 and said clips 107 are locked in said horizontal configuration, holding said implant attached to said frame arm 104.

It should be pointed out that it is a unidirectional mechanism. In other words, if one tries to force clips 107 to its vertical configuration, locking tabs 202 will 'bump into locking bar 203.

Figure 3D:
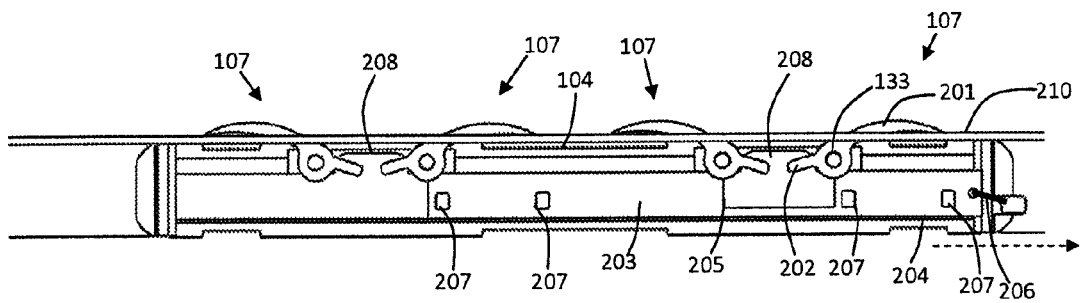
Figure 3E:
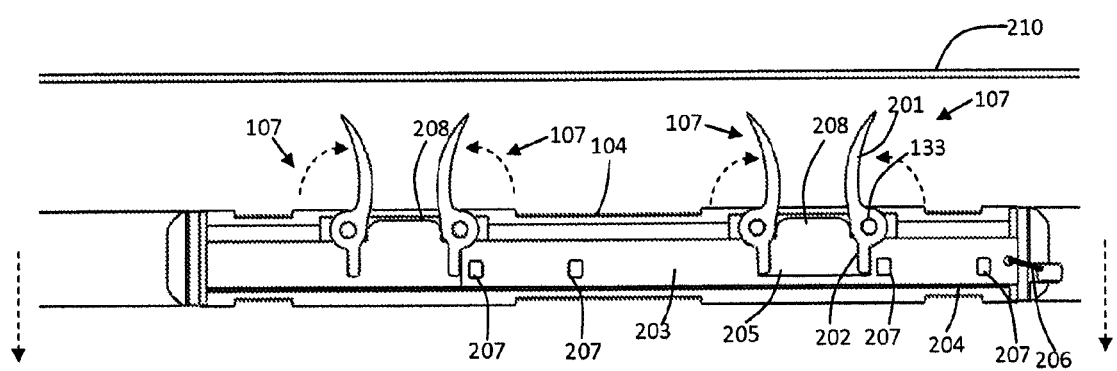

By further pulling said locking bar 203 towards the proximal portion the clips 107 are unlocked and can be rotated be back to its vertical configuration (see FIGS. 3D and 3E).

Once detachment between said implant 210 and said implant deployment device in desired, locking bar 203 is pulled backward by wire 206, changing the position of said locking bar form its said lock position into its said free position (see FIG. 3D). In said free position of the locking bar 203, the clips 107 are free to rotate (hence, as will be discussed hereinafter, a detachment between the implant deployment device and the implant is enabled).

Once locking bar 203 is positioned in said free position, said groove's 205 is located below said clips 107, therefore said locking bar 202 is no longer limiting the movement of said clips 107 enabling their free movement. In this state, detachment can be obtained by simply pulling said frame arm 104 away from said implant; as a result, said clips 107 rotate back into their said vertical configuration and are released from said implant (see FIG. 2E).

Reference is now made to FIG. 4A-4H, which illustrate an embodiment of a stapling apparatus 400 adapted for providing said reversible connection by said active reversible connection mechanism. Said stapling apparatus 400 comprises a frame 401 which holds the distal portion 101 of an implant deployment device 100. Four staplers 403 are connected to the frame 401 at each cornet by four separate hinges (either standard or living hinges). Each said stapler 403 is adapted to push down the implant 210 through a pair of clip 107 and to transform said clips 107 from a vertical position into a horizontal position (thus providing said reversible connection). Stapling presses 404 are located at the end of each stapler inside groove 405 and adapted to push clip 107 into horizontal position. Each pair of staplers 403 is connected via bridge 407 in order to prevent lateral movement of said staplers 403 during the stapling process. A snap groove 406 is located at the center of the frame 401 and adapted to reversibly hold said implant deployment device 100 attached to stapling apparatus 400 until said reversible attachment is obtained.

Figure 4A:
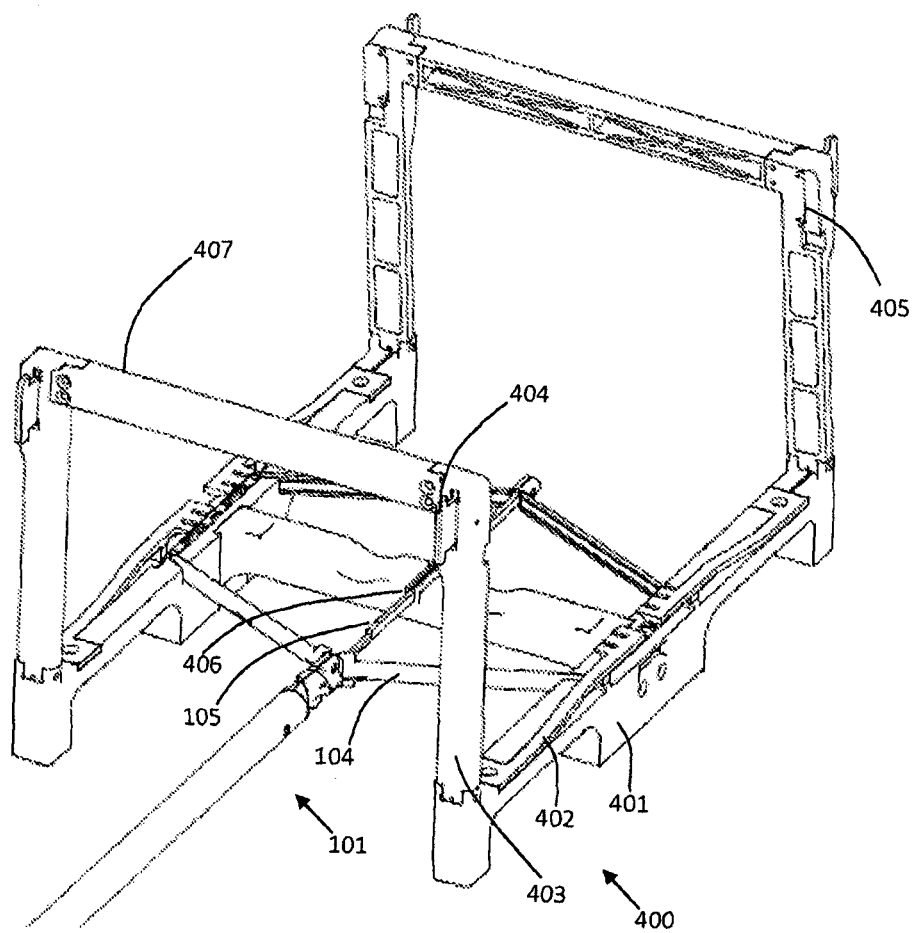
FIG. 4A-4H illustrate an embodiment of a stapling apparatus adapted for providing a reversible connection by the active reversible connection mechanism.
Figure 4B:
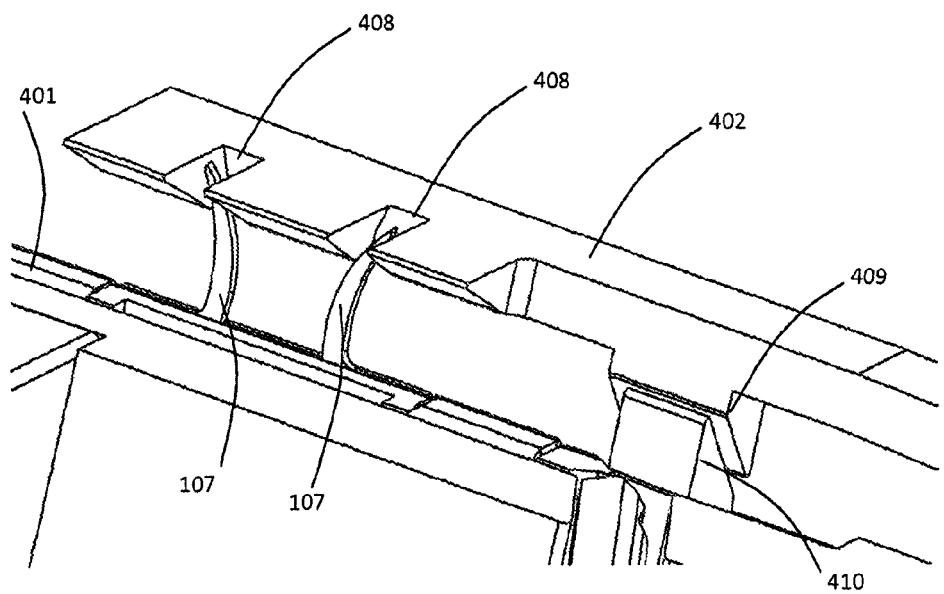
Figure 4C:
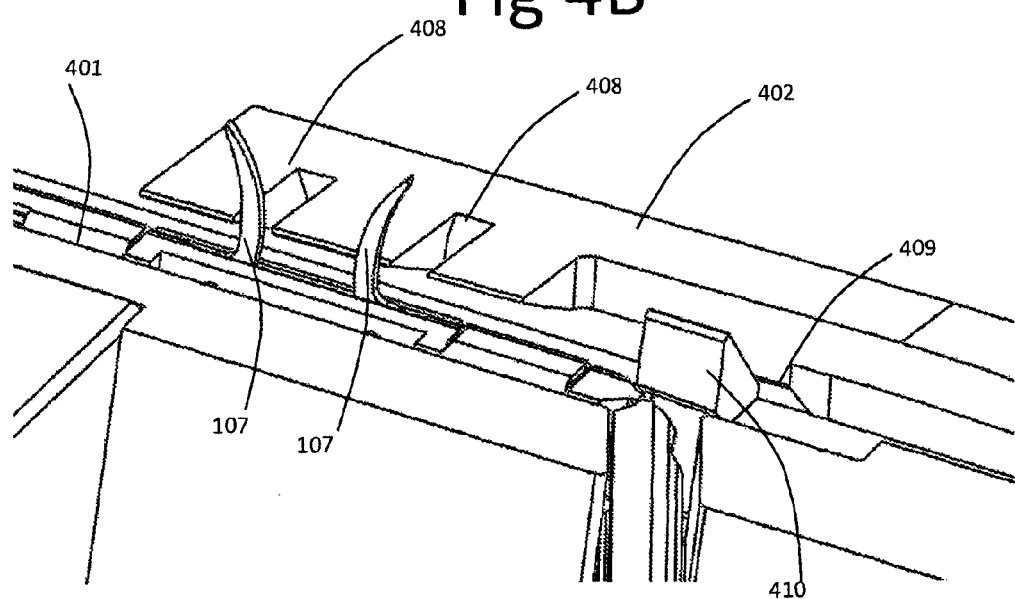
Figure 4D:
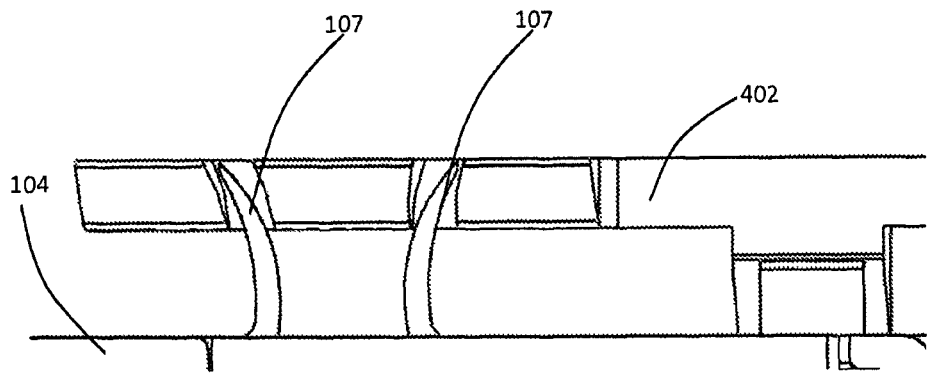
Figure 4E:
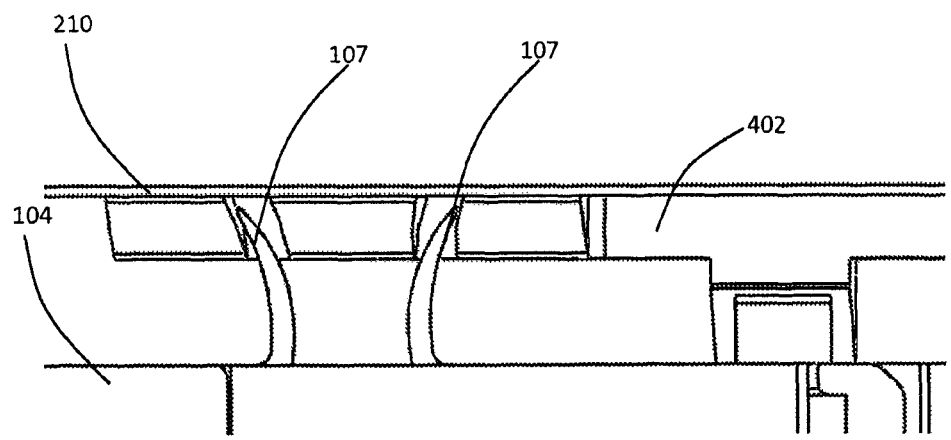

Each pair of clip 107 is held in a vertical position by clip holder 402. Each said clip holder 402 is adapted to hold a pair of clip 107 in vertical position in order to allow its insertion through the implant 210 during the stapling process. In addition, clip holder 402 is adapted the hold the clips vertical during shipment in order to allow stapling in the operation room without the need of any preparation. As illustrated in FIGS. 4B-4C, each clip holder 402 comprises two grooves 408 which hold the clip 107 in a vertical position. Once stapling process is performed and the surgeon is lowering the stapler 403 toward the implant, each clip holder 402 is pushed down and as a result it is also moving laterally. In this state, since the clip 107 are extracted from groves 408, their transformation from vertical into horizontal position is enabled; said lateral movement of said clip holder 402 is obtained as bulge 409 at clip holder 402 is sliding along bulge 410 at the stapling frame 401 during the down movement of clip holder 402.

Figure 4F:
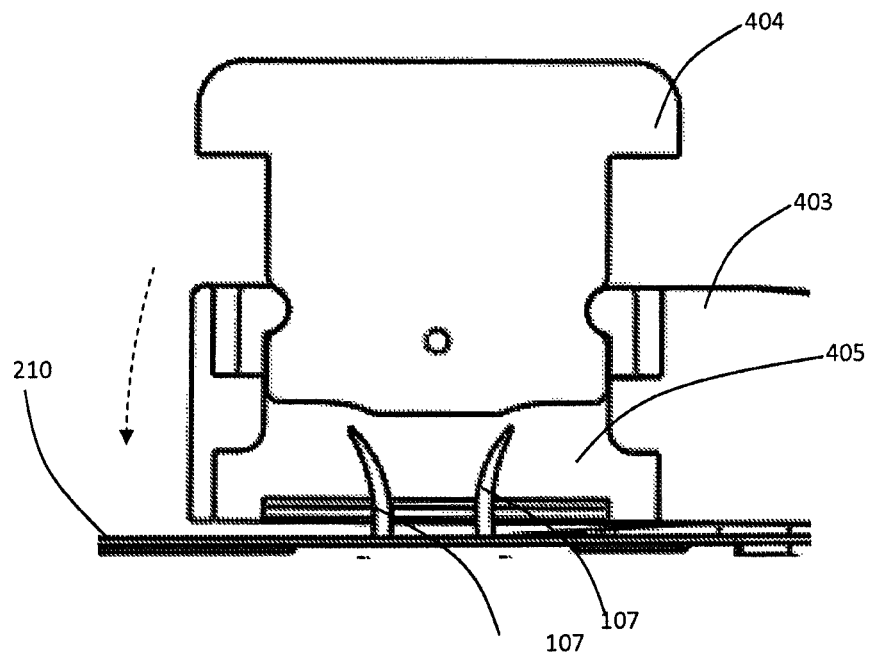
Figure 4G:
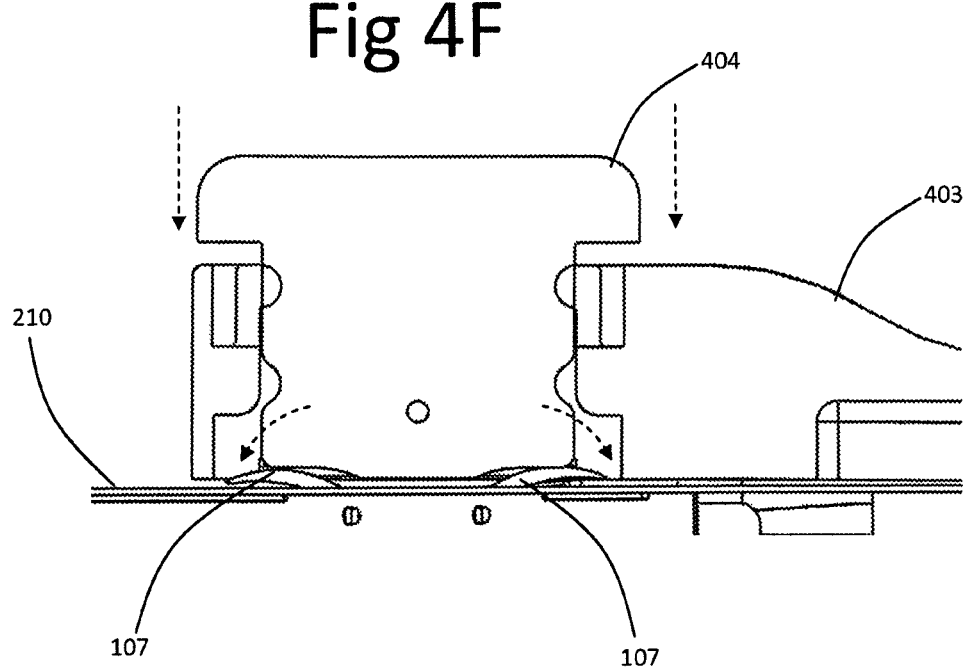

FIGS. 4D-4G illustrate the process of connecting the implant 210 to one pair of clip. At the initial stage (FIG. 4D), the clips are held vertically by clip holder 402. Next, an implant 210 is places on top of the stapling apparatus (FIG. 4E); the stapler 403 is then lowered toward the implant 210 by the surgeon (or other member of the medical staff); as a result the two clip 107 are penetrating through implant 210 and into groove 405 (FIG. 4F). During the initial penetration, clip 107 is held by clip holder 402, thus premature transformation from vertical into horizontal position is prevented. Once the clip 107 are completely inserted into said implant 210, clip holder 402 is positioned laterally relative to the clip 107 (as also described is FIGS. 4B-4C); at this stage the surgeon push on stapler press 404 and lower it toward clip 107 (FIG. 4G), as a result clip 107 position is transformed form vertical position into horizontal position. Since the said lock bar 203 is located at its said lock position, once clip 107 are substantially horizontal position, they are locked in this stage, thus providing said reversible connection between implant 210 and implant deployment device 100. Once said connection is obtain with all clip 107, implant deployment device is removed from SA 400.

Figure 4H:
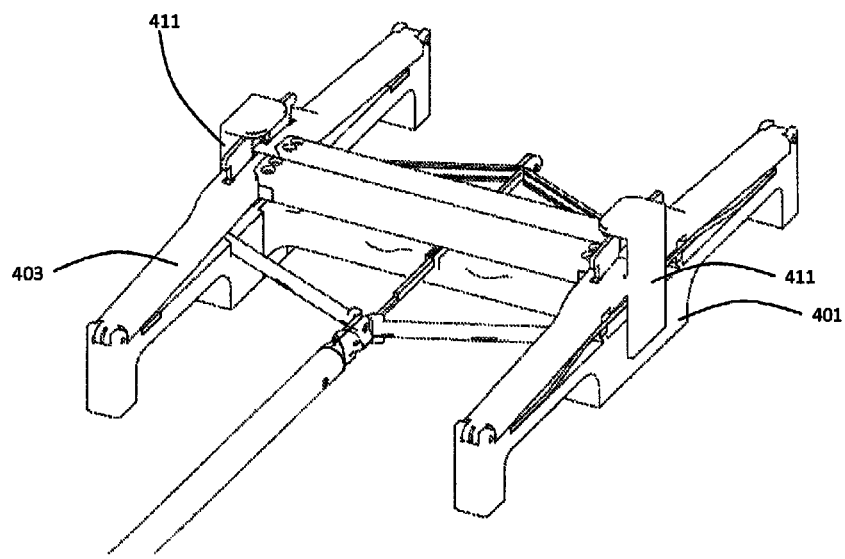

FIG. 4H illustrates the configuration of stapling apparatus 400 during shipment. In order to reduce package volume during shipment and to keep the device ready for stapling, at least one, preferably two, packaging caps 411 are utilized. Said caps 411 are reversibly attached to the frame 401, and adapted to retain stapler 403 in a substantially horizontal position during device shipment. In addition, said caps 411 also prevent down movement of stapler press 404, prevent lateral movement of clip holder 402 and prevent non-deliberate extraction of implant deployment device 100 from frame 401.

Once the device in removed from its packaging during the surgery, said pack caps 411 are removed by the medical staff in order to allow stapling of the implant 210 to the implant deployment device 100. Once the caps 411 are removed, the staplers 403 springs into horizontal position allowing the placement of implant 210 onto the stapling apparatus 400 and implant deployment device 100.

In order to allow tight spreading of the implant 210 during surgery, said stapling process is preformed while implant deployment device 100 is not completely opened; as a result, once implant deployment device is completely opened inside the abdominal cavity, it is stretched beyond its original dimension (as was during stapling) therefore tight spreading is obtained.

Figure 5:
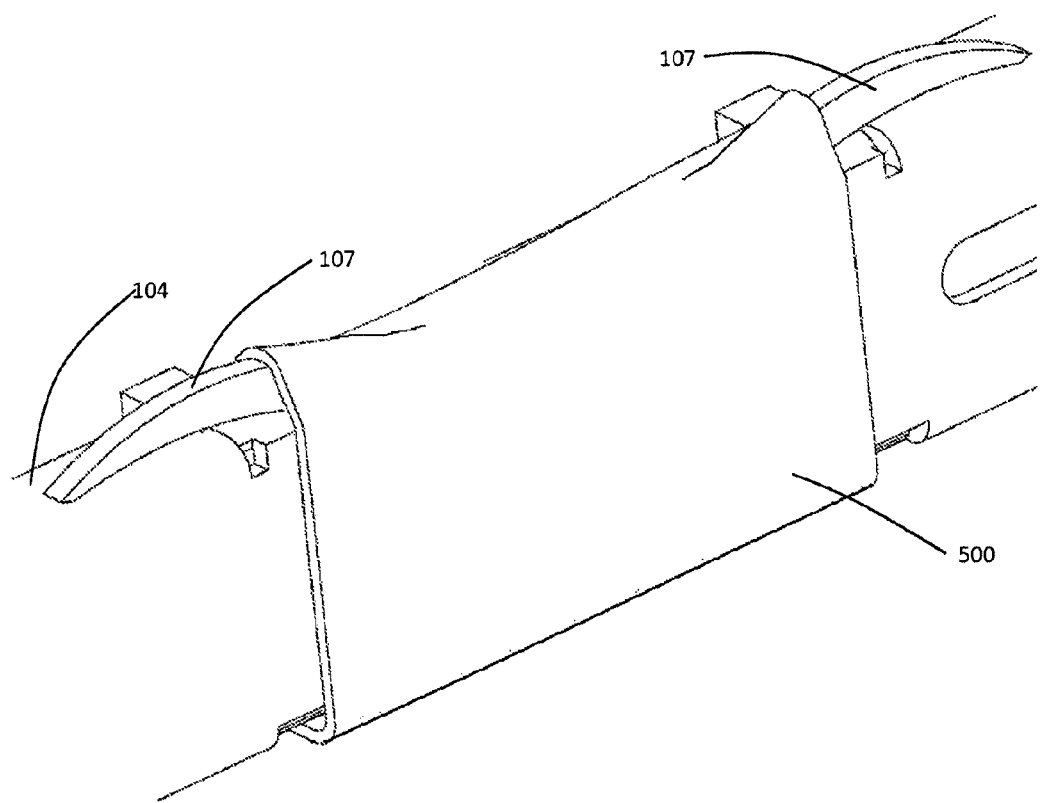
FIG. 5 illustrates an embodiment of a staple return spring.

Reference is now being made to FIG. 5 which illustrates an embodiment of a staple return spring 500. In general, staple return spring 500 is needed in order to return clip 107 into horizontal position immediate after detachment from the implant 210; this is necessary in order prevent damage to internal organs by the sharp tip of clip 107 and in order to prevent clip 107 from being caught at the trocar or at the tissue during device extraction.

Figure 6A:
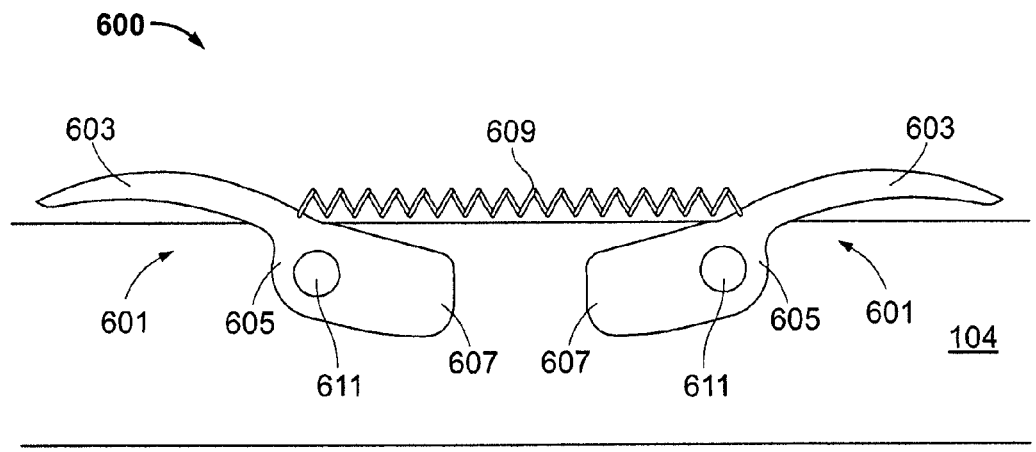
FIGS. 6A and 6B illustrate an embodiment of a clip spring system in accordance with the present disclosure in a closed position and an open position, respectively.
Figure 6B:
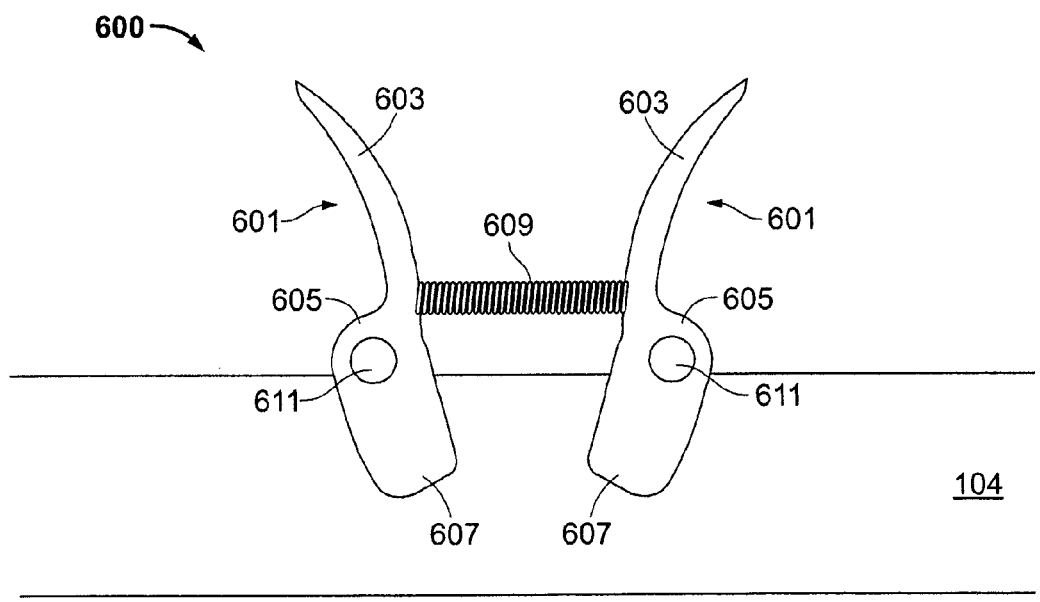

Referring to FIGS. 6A and 6B, an embodiment of a clip spring system 600 for use with an implant deployment device 100 (FIG. 1) is illustrated. Clip spring system 600 includes two clips 601, each clip 601 including a hook 603, similar to the protruding portion 201 of FIG. 2 as described above, a body 605 having a locking portion 607 similar in function to the locking tab 202 of FIG. 2 as described above, and a hinge hole 611 similar to the hinge holes 133 of FIG. 2 as described above. The clip spring system 600 also includes a spring member 609 operably connected to each clip 601, and configured to provide a restoring force due to material deformation of the spring member 609 to move the clips 601 from an open position (FIG. 6B) to a closed position (FIG. 6A). That is, the spring member 609 biases the clips 601 towards the closed position. As herein described with respect to this and future embodiments, an open position is any position where the hooks as herein described are not in contact with or in close proximity to the frame arm 104, and a closed position is where the hooks are in contact with or in close proximity to the frame arm to secure an implant to the frame arm. The spring member 609 may take any suitable shape capable of providing a spring force against the clips 601 when at least one of the hooks 603 is rotated upwards and away from the frame arm 104. As shown in FIGS. 6A and 6B, spring member 609 is a single coiled spring attached to the clips 601, however, more than one spring may be used. Also, a torsion spring or coiled spring may be used instead of a linear spring. For example, one or more torsion springs may be inlayed in one or more of the hinge holes 611 such that the spring restores the clips 601 to the closed position. The spring member 609 may be made from any suitable semi-rigid material, including but not limited to one or more of a metal, polymer, plastic, and/or shape memory material such as nitinol.

Figure 7A:
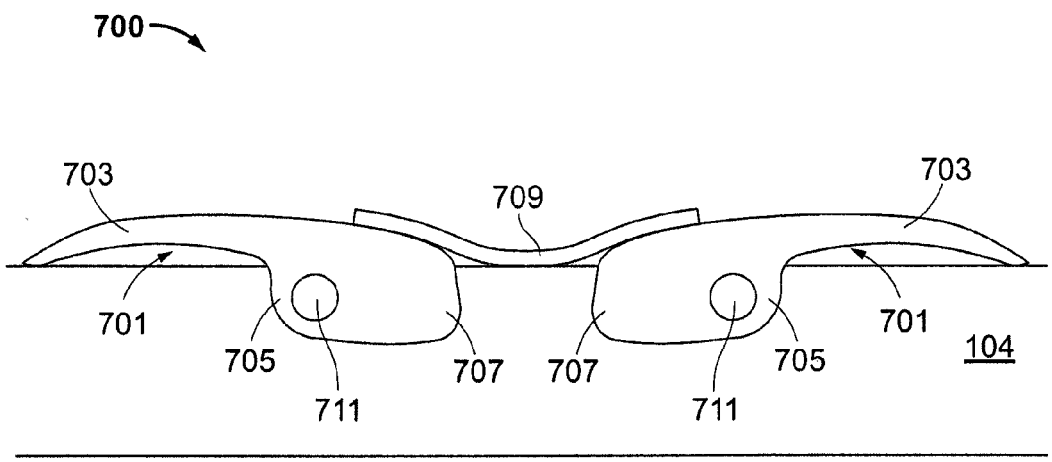
FIGS. 7A and 7B illustrate an embodiment of a clip spring system in accordance with the present disclosure in a closed position and an open position, respectively.
Figure 7B:
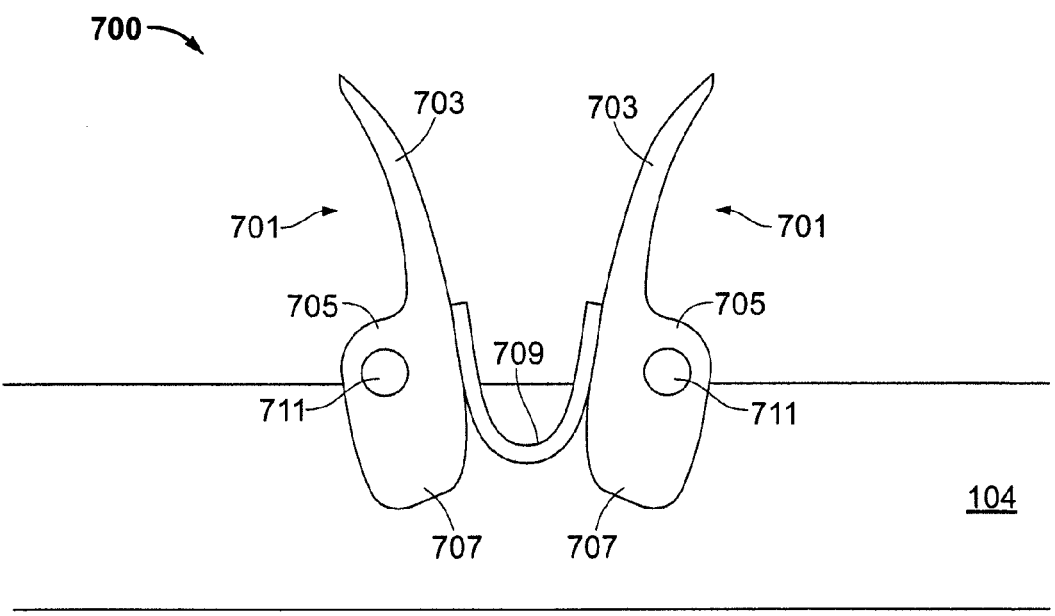

Referring to FIGS. 7A-7C, an embodiment of a clip spring system 700 for use with an implant deployment device 100 is illustrated. Clip spring system 700 includes two clips 701, each clip 701 including a hook 703, similar to the protruding portion 201 of FIG. 2 as described above, a body 705 having a locking portion 707 similar in function to the locking tab 202 of FIG. 2 as described above, and a hinge hole 711 similar to the hinge holes 133 of FIG. 2 as described above. The clip spring system 700 also includes a spring member 709 operably connected to each clip 701, and configured to provide a restoring force to move the clips 701 from an open position (FIG. 7B) to a closed position (FIG. 7A). That is, the spring member 709 biases the clips 701 towards the closed position. The spring member 709 may take any suitable shape capable of providing a spring force against the clips 701 when at least one of the hooks 703 is rotated upwards and away from the frame arm 104. As shown in FIGS. 7A-7C, spring member 709 operably contacts an upper surface of each clip 701 of the clip spring system 700, and is generally U-shaped when under tension from the clips 701 being rotated into the open position (FIG. 7B). Spring member 709 may further include an integral or removable anchor portion 713 (FIG. 7C) that connects to the frame arm 104. The spring member 709 may be formed from a single piece of material, such as, but not limited to, a single sheet of material. The spring member 709 may be made from any suitable semi-rigid material, including but not limited to one or more of a metal, polymer, plastic, and/or shape memory material such as nitinol.

Figure 8A:
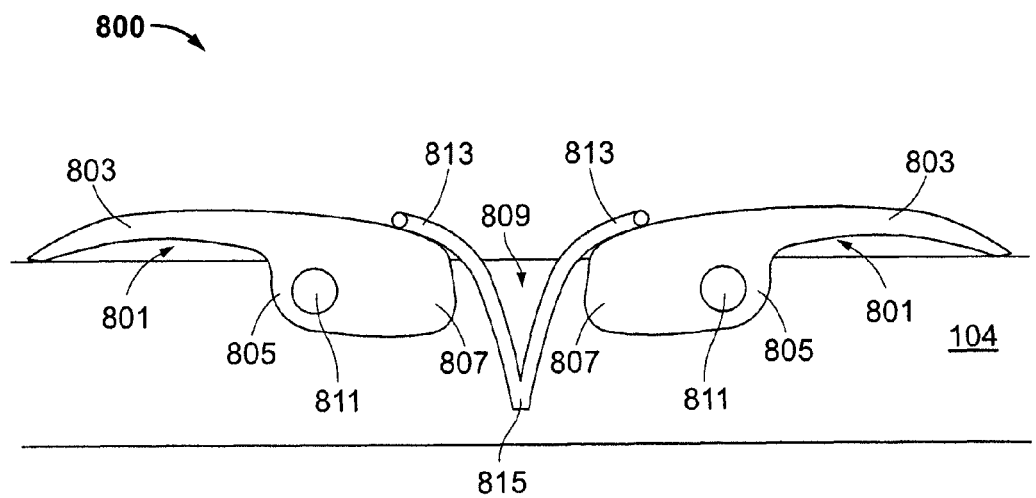
FIGS. 8A and 8B illustrate an embodiment of a clip spring system in accordance with the present disclosure.
Figure 8B:
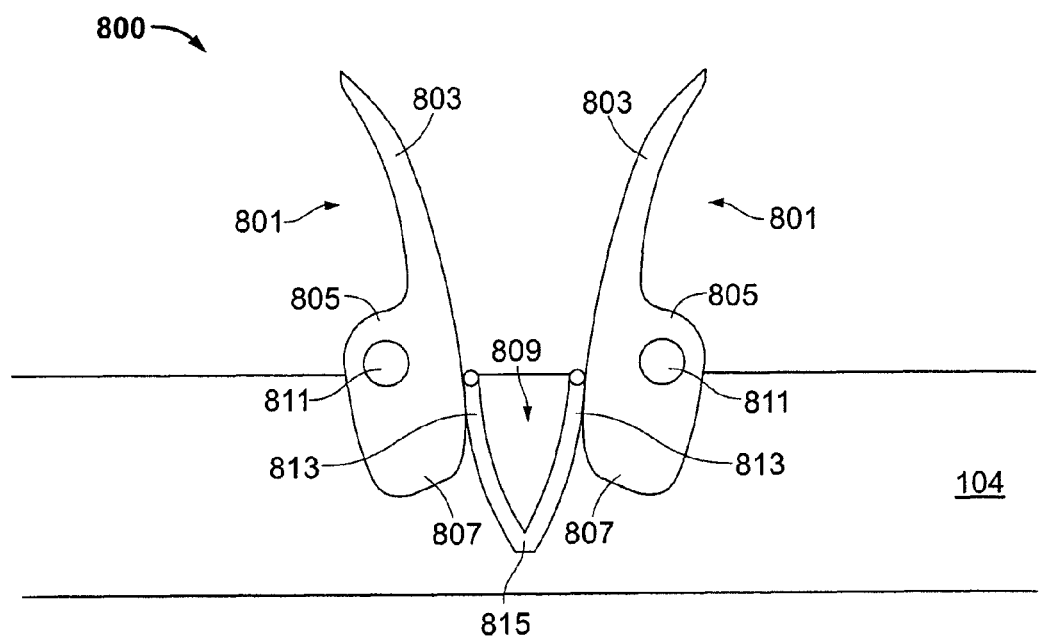

Referring to FIGS. 8A and 8B, an embodiment of a clip spring system 800 for use with an implant deployment device 100 is illustrated. Clip spring system 800 includes two clips 801, each clip 801 including a hook 803, similar to the protruding portion 201 of FIG. 2 as described above, a body 805 having a locking portion 807 similar in function to the locking tab 202 of FIG. 2 as described above, and a hinge hole 811 similar to the hinge holes 133 of FIG. 2 as described above. The clip spring system 800 also includes a spring member 809 slidably engaged with each clip 801, and configured to provide a restoring force to move the clips 801 from an open position (FIG. 8B) to a closed position (FIG. 8A). That is, the spring member 809 biases the clips 801 towards the closed position. The spring member 809 may take any suitable shape capable of providing a spring force against the clips 801 when at least one of the hooks 803 is rotated upwards and away from the frame arm 804. As shown in FIGS. 8A and 8B, spring member 809 includes at least one bendable arm 813 slidably contacting at least one of the clips 801 and an anchor portion 815 fixed to the frame arm 104. The spring member 809 includes a V-shape that allows arms 813 to be bent toward each other, thereby creating a restoring force on clips 801 as a function of material resistance of the arms 813. As shown, the arms 813 are slidably connected to a top surface of body 805 or hook 803 of each clip 801 of the clip spring system 800. The spring member 809 may be made from any suitable semi-rigid material, including but not limited to one or more of a metal, polymer, plastic, and/or shape memory material such as nitinol.

Figure 9A:
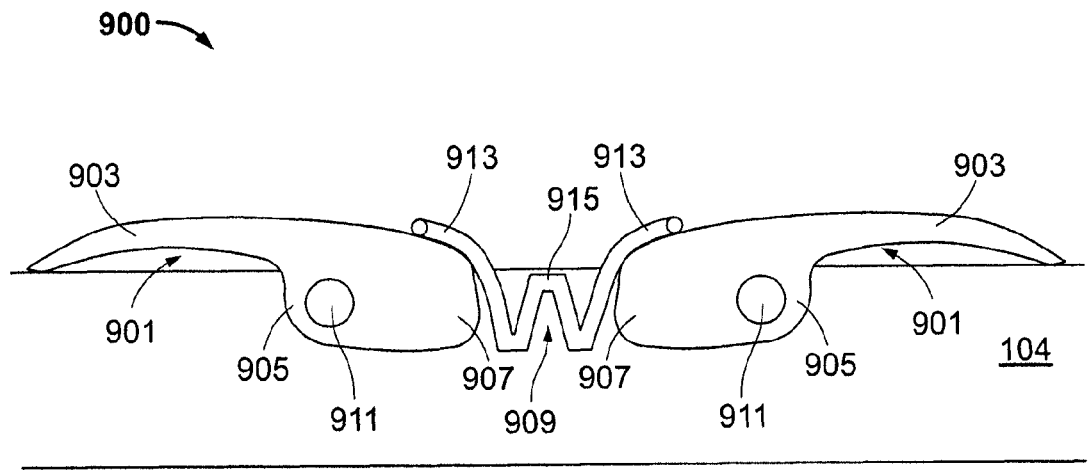
FIGS. 9A and 9B illustrate an embodiment of a clip spring system in accordance with the present disclosure in a closed position and an open position, respectively.
Figure 9B:
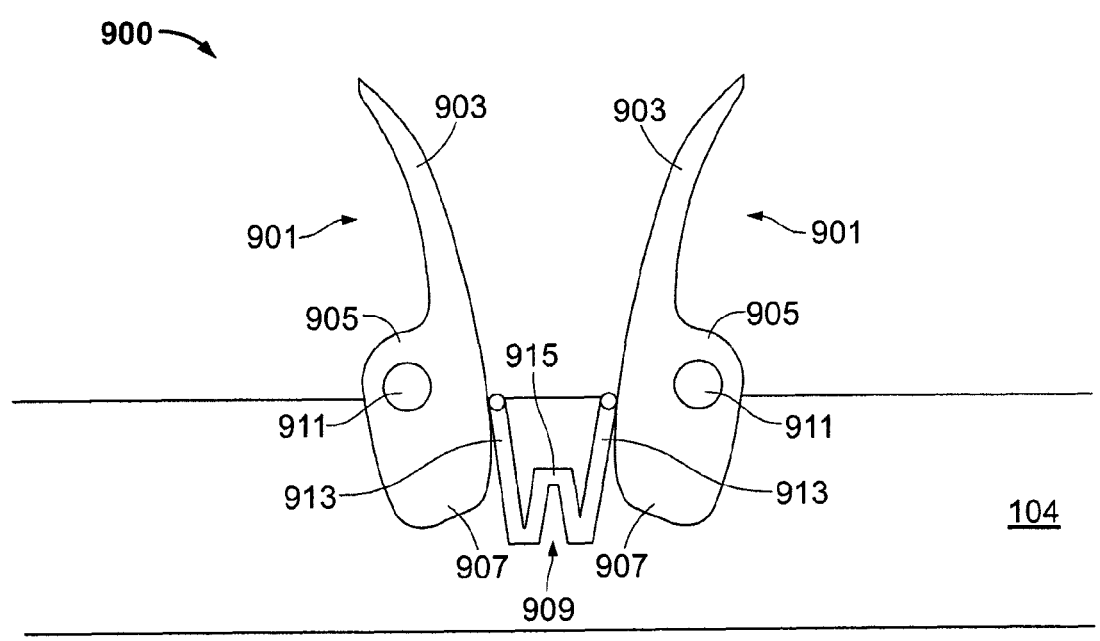
Figure 9C:
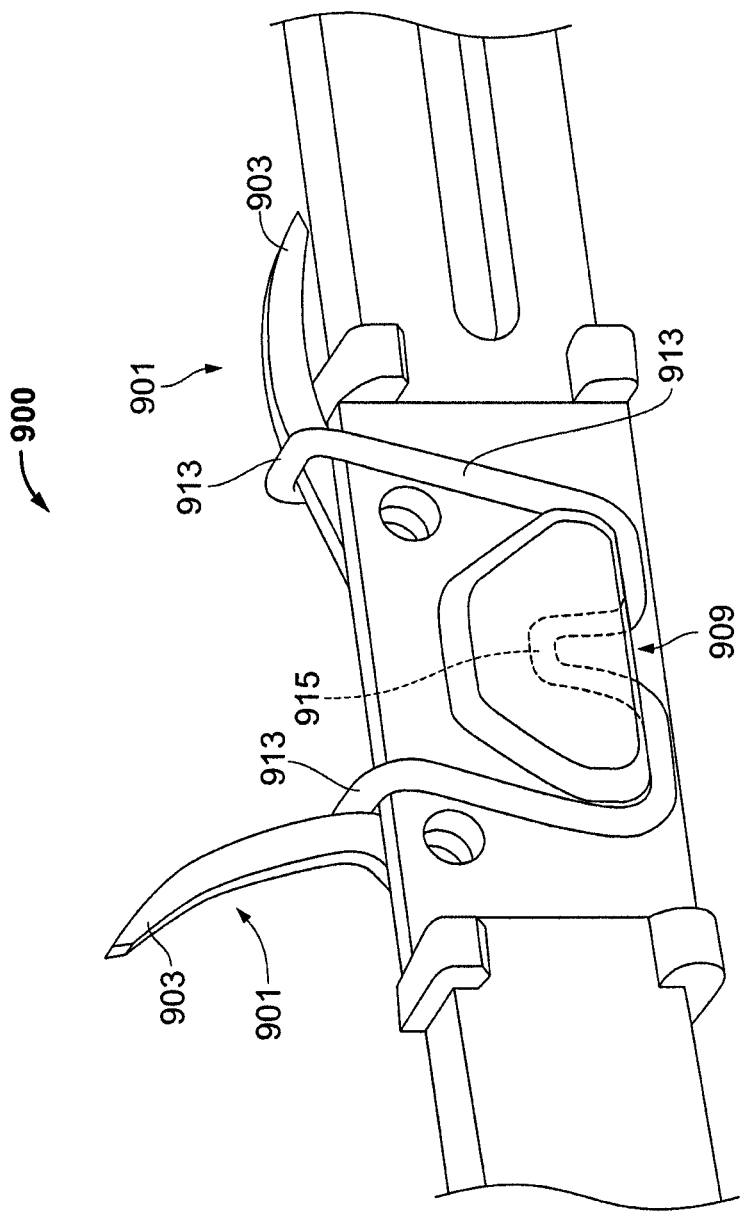
FIG. 9C is a perspective view of the embodiment of FIGS. 9A and 9B having one clip in a closed position and another clip in an open position.

Referring to FIGS. 9A-9C, an embodiment of a clip spring system 900 for use with an implant deployment device 100 is illustrated. Clip spring system 900 includes two clips 901, each clip 901 including a hook 903, similar to the protruding portion 201 of FIG. 2 as described above, a body 905 having a locking portion 907 similar in function to the locking tab 202 of FIG. 2 as described above, and a hinge hole 911 similar to the hinge holes 133 of FIG. 2 as described above. The clip spring system 900 also includes a spring member 909 slidably contacting each clip 901, and configured to provide a restoring force to move the clips 901 from an open position (FIG. 9A) to a closed position (FIG. 9A). That is, the spring member 909 biases the clips 901 towards the closed position. The spring member 909 may take any suitable shape capable of providing a spring force against the clips 901 when at least one of the hooks 903 is rotated upward away from the frame arm 904. As shown in FIGS. 9A and 9B, spring member 909 includes at least one bendable arm 913 slidably attached to at least one of the clips 901 and an anchor portion 915 fixed to the frame arm 104. The bendable member includes a W-shape that allows arms 913 to be bent toward each other, thereby creating a restoring force on clips 901 as a function of material resistance of the arms 913. As shown, the arms 913 are slidably connected to a top surface of body 905 or hook 903 of each clip 901 of the clip spring system 900. Referring specifically to FIG. 9C, the anchor portion 915 may be disposed on the opposite side of the frame arm 104 as the clips 901, and may also be at least partially covered by frame arm 104. The spring member 909 may be made from any suitable semi-rigid material, including but not limited to one or more of a metal, polymer, plastic, and/or shape memory material such as nitinol.

The herein described spring members may be configured to communicate with a bottom surface of the clips such that the spring member is biased move the clips to the closed position by applying a force to the lower surface of the clip, or an extension disposed on a bottom surface of the clip as shown in FIGS. 10A-11B.

Figure 10A:
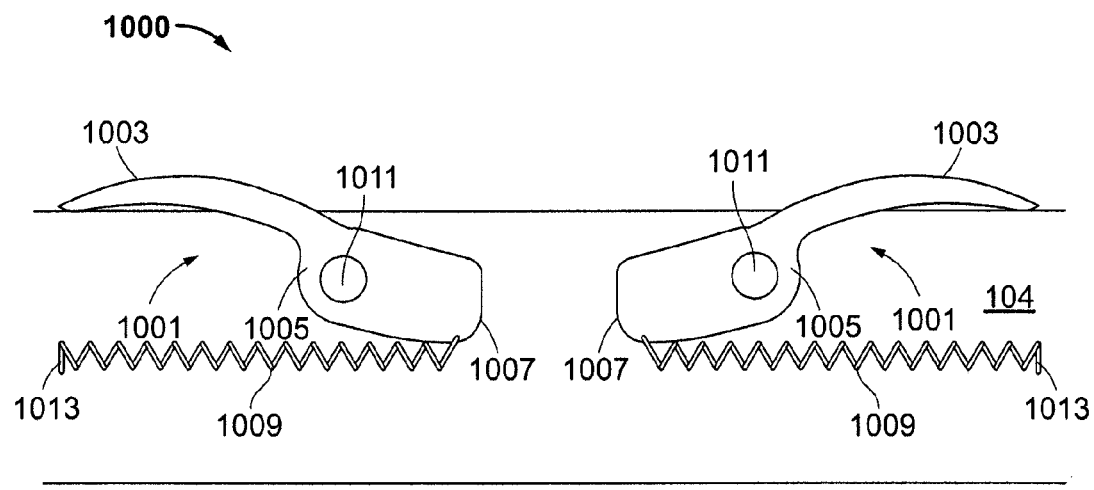
FIGS. 10A and 10B illustrate an embodiment of a clip spring system in accordance with the present disclosure in a closed position and an open position, respectively.
Figure 10B:
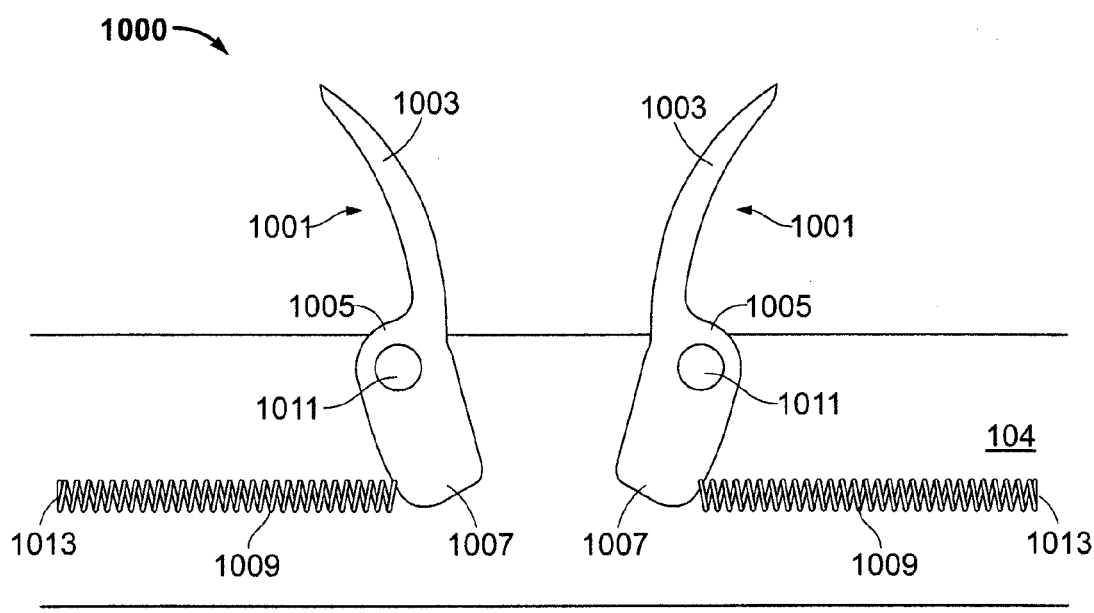

Referring to FIGS. 10A and 10B, an embodiment of a clip spring system 1000 for use with an implant deployment device 100 is illustrated. Clip spring system 1000 includes two clips 1001, each clip 1001 including a hook 1003, similar to the protruding portion 201 of FIG. 2 as described above, a body 1005 having a locking portion 1007 similar in function to the locking tab 202 of FIG. 2 as described above, and a hinge hole 1011 similar to the hinge holes 133 of FIG. 2 as described above. The clip spring system 1000 also includes a spring members 1009 operably connected to each clip 1001, and configured to provide a restoring force to move the clips 1001 from an open position, as shown in FIG. 10B, to a closed position, as shown in FIG. 10A. That is, the spring member 1009 biases the clips 1001 towards the closed position. The spring member 1009 may take any suitable shape capable of providing a spring force against the clips 1001 when at least one of the hooks 1003 is rotated upwards and away from the frame arm 104. As shown in FIGS. 10A and 10B, spring members 1009 are a single coiled spring attached to the clips 1001 at a lower surface of the clips 1001. Each spring member 1009 is attached to the frame arm 104 at an anchor point 1013. The spring member 1009 may be made from any suitable semi-rigid material, including but not limited to one or more of a metal, polymer, plastic, and/or shape memory material such as nitinol.

Figure 11A:
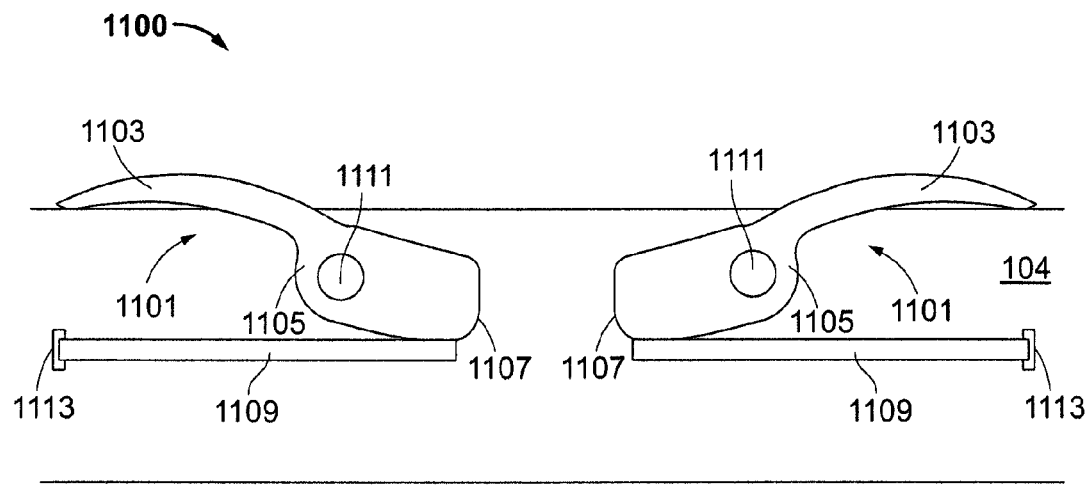
FIGS. 11A and 11B illustrate an embodiment of a clip spring system in accordance with the present disclosure in a closed position and an open position, respectively.
Figure 11B:
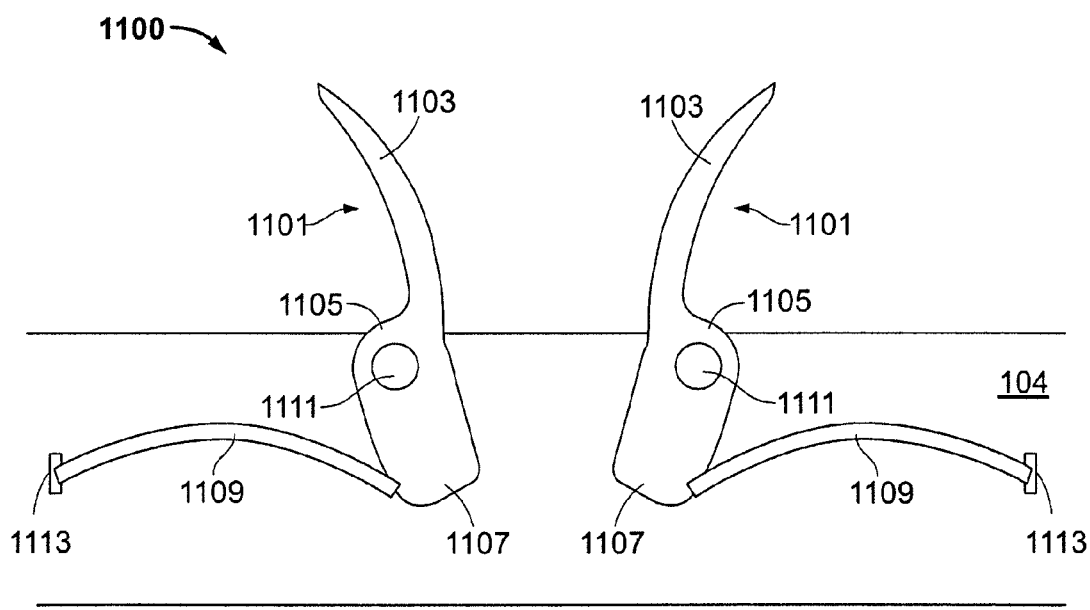

Referring to FIGS. 11A and 11B, an embodiment of a clip spring system 1100 for use with an implant deployment device 100 is illustrated. Clip spring system 1100 includes two clips 1101, each clip 1101 including a hook 1103, similar to the protruding portion 201 of FIG. 2 as described above, a body 1105 having a locking portion 1107 similar in function to the locking tab 202 of FIG. 2 as described above, and a hinge hole 1111 similar to the hinge holes 133 of FIG. 2 as described above. The clip spring system 1100 also includes a spring members 1109 operably connected to each clip 1101, and configured to provide a restoring force to move the clips 1101 from an open position, as shown in FIG. 11B, to a closed position, as shown in FIG. 11A. That is, the spring member 1109 biases the clips 1101 towards the closed position. The spring member 1109 may take any suitable shape capable of providing a spring force against the clips 1101 when at least one of the hooks 1103 is rotated upwards and away from the frame arm 104. As shown in FIGS. 11A and 11B, spring members 1109 are bendable arms attached to the clips 1101 at a lower surface of the clips 1101. Each spring member 1109 is either fixedly or rotatably attached to the frame arm 104 at an anchor point 1113. The spring members 1109 are shown as separate members anchored to the frame arm 104, but one ordinarily skilled would appreciate that the arms may be linked together in a manner similar to the V-type or W-type spring members as described herein, and configured to be attached to a bottom surface of the clips 1101. The spring member 1109 may be made from any suitable semi-rigid material, including but not limited to one or more of a metal, polymer, plastic, and/or shape memory material such as nitinol.

Figure 12:
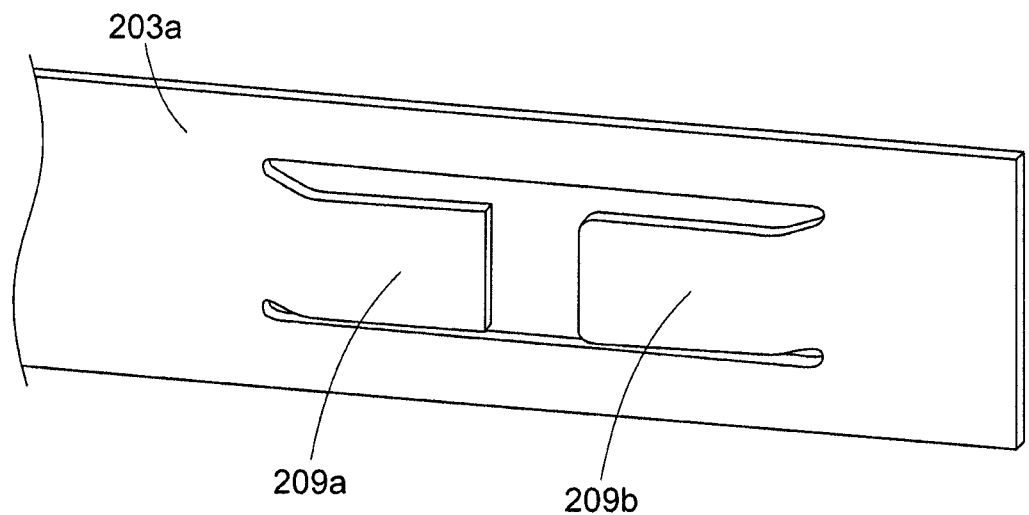
FIG. 12 is a perspective view of a lock bar according to an embodiment of the present disclosure.

Referring to FIG. 12, another embodiment of a lock bar 203a for use with an implant deployment device 100 is illustrated. As shown, lock bar 203a includes protrusions 209a, 209b formed from or attached to lock bar 203a that extend at least partially away from the lock bar 203a in a lateral direction that is away from the frame arm 104. Each protrusion 209a, 209b may be a tab of material that is cut out of the lock bar 203a and bent outwardly to create a ramp-like cammed shaped as shown in FIG. 12. Each protrusion 209a, 209b may also be a separate piece permanently or releasably attached to the lock bar 203a.

Figure 13A:
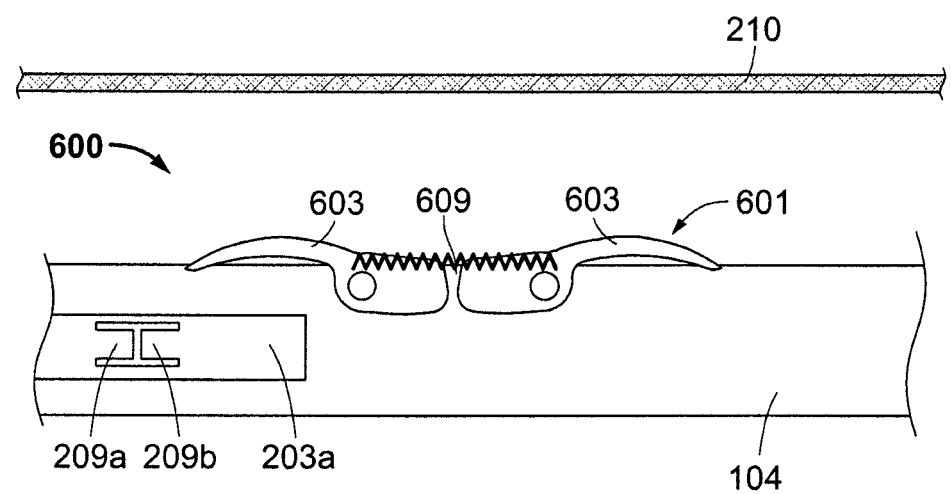
FIG. 13A is a perspective view of the clip spring system of FIG. 6A in the closed position and the lock bar of FIG. 12 in an unlocked position.
Figure 13B:
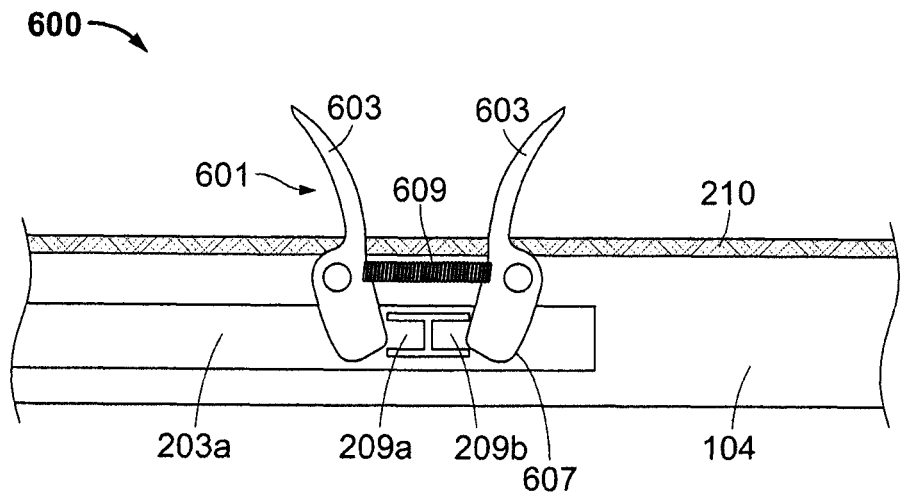
FIG. 13B is a perspective view of the clip spring system of FIG. 6A in the open position and the lock bar of FIG. 12 in a locked position.
Figure 13C:
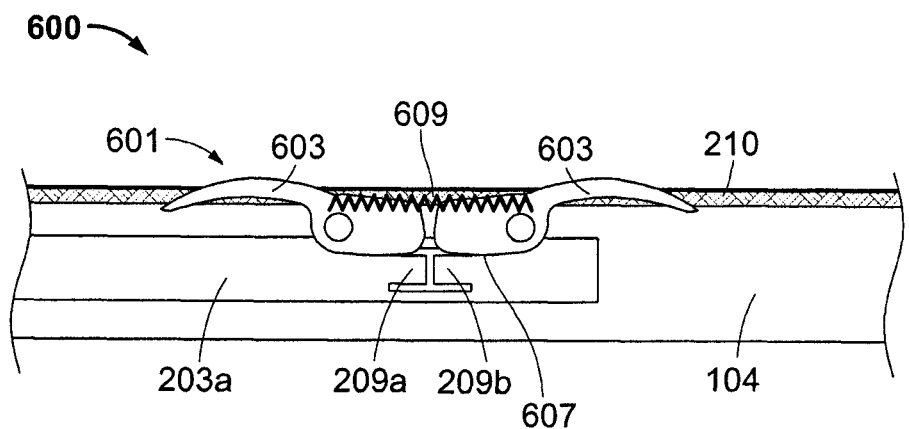
FIG. 13C is a perspective view of the clip spring system of FIG. 6A in the closed position and the lock bar of FIG. 12 in the locked position.

Although the lock bar 203a will discussed with respect to the clip spring system 600 that is shown in FIGS. 6A and 6B, the lock bar 203a is usable with any of the clip spring systems disclosed herein. Referring now to FIG. 13A, the frame arm 104 includes the lock bar 203a and the clip spring system 600. The lock bar 203a is shown in an unlocked position and the clip spring system 600 is shown in the closed position. The clips 601 are rotatable to the open position, as seen in FIG. 13B, which allows the clinician to attach the surgical implant 210 (FIG. 3A) to the frame arm 104 by passing the surgical implant 210 over the hooks 603 of the clips 601. This is the default configuration for the implant deployment device 100 since it allows the clinician to attach the surgical implant 210 to the implant deployment device 100 since the clips 601 are maintained in the open position due to the interaction with the clips 601 and the lock bar 203a in the locked position (FIG. 13B). Once the surgical implant 210 is abutting the frame arm 104, the clips 601 are rotated to the closed position over the protrusions 209a, 209b of the lock bar 203 as shown in FIG. 13C. With the clips 601 in the closed position and the lock bar 203a in the locked position, the locking portions 607 of the clips 601 contact upper surfaces of the protrusions 209a, 209b of the lock bar 203a, thereby maintaining the clips 601 in the closed position Utilizing one or more embodiments of clip spring systems as herein disclosed causes a biasing to the clips such that the hook portions of the clips tend to push up against the frame arm 104 and hold down any mesh attached thereto. The operation of the implant deployment device 100 will be discussed with respect to FIGS. 13A-13C, but it is within the scope of the present disclosure that the lock bar 203a may be used with any disclosed embodiment of the clip spring system. The clips may be initially locked in an open position (e.g. FIG. 13B) allowing a clinician to pass the surgical implant 210 (e.g. a surgical mesh) over the hooks 603 of the clip 601 and place the surgical implant 210 against the frame arm 104. After the surgical implant 210 has been coupled to the implant deployment device 100 using the hooks 603, the clinician secures the surgical implant 210 to the implant deployment device 100 by rotating the clips 601 from the open and locked position (FIG. 13B) to the closed and locked position (FIG. 13C). In this configuration, the implant deployment device 100 is ready for use. When deployment of the surgical implant 210 is desired, the clinician positions the implant deployment device 100 in a surgical site and maneuvers the surgical implant 210 into a desired location (e.g. hernia). With the surgical implant 210 in the desired location, the clinician affixes the surgical implant 210 to body tissue using known techniques. Subsequently, the clinician actuates a release button (not shown) on the mesh deployment device 100, which translates the lock bar 203a from the locked position (FIG. 13A) to the unlocked position (FIG. 13A). With the lock bar 203a in the unlocked position, the clinician moves the implant deployment device 100 away from body tissue. Since the surgical implant 210 is affixed to body tissue, movement of the implant deployment device 100 and consequential movement of the frame arm 104, separates the frame arm 104 from the surgical implant 210 and causes concurrent rotation of the clips 601 from the closed position to the open position. Thus, the surgical implant 210 remains affixed to body tissue in the surgical site and the implant deployment device 100 is separated from the surgical implant 210. Prior to removing the implant deployment device 100 from the surgical site, the clinician allows the spring bias of the spring member 609 to rotate the clips 601 from the open position to the closed position. Once the clips 601 are in the closed position, the clinician removes the implant deployment device 100 from the surgical site.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A surgical instrument comprising: a proximal portion including a handle;
   a distal portion extending from the handle and adapted to be inserted into a body, the distal portion including a frame arm having a hinge tab;
   a clip pivotally secured to the frame arm, the clip defining a hinge hole, wherein the hinge tab is received through the hinge hole to rotatably support the clip about the hinge tab between an open position and a closed position, the clip configured to releasably retain a surgical implant;
   a lock bar operatively associated with the frame arm, the lock bar translatable along a longitudinal axis of the frame arm between a locked position and an unlocked position, the lock bar maintaining the clip in one of the open position or the closed position when the lock bar is in the locked position; and
   means for transitioning the clip from the open position to the closed position, the means for transitioning the clip includes a spring member operatively coupled to the clip.

2. The surgical instrument of claim 1, wherein the means for transitioning the clip urges the clip from the open position to the closed position when the lock bar is in the unlocked position.

3. The surgical instrument of claim 1, further including an implant attachable to the frame arm.

4. The surgical instrument of claim 3, wherein the implant is retained to the frame arm when the clip is in the closed position.

5. The surgical instrument of claim 3, wherein the means for transitioning the clip urges the clip from the open position to the closed position when the lock bar is in the unlocked position.

6. The surgical instrument of claim 3, wherein the clip remains in one of the closed or open positions when the lock bar is in the locked position.

7. The surgical instrument of claim 1, further including a cover, wherein the hinge tab extends from the cover.

* * * * *